United States Patent
Inoue et al.

(10) Patent No.: US 11,266,369 B2
(45) Date of Patent: Mar. 8, 2022

(54) RADIOGRAPHY SYSTEM, CONTROL METHOD, AND CONTROL PROGRAM

(71) Applicant: FUJIFILM Corporation, Tokyo (JP)

(72) Inventors: Tomoki Inoue, Kanagawa (JP); Hiroki Nakayama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 185 days.

(21) Appl. No.: 16/798,442

(22) Filed: Feb. 24, 2020

(65) Prior Publication Data

US 2020/0275902 A1 Sep. 3, 2020

(30) Foreign Application Priority Data

Feb. 28, 2019 (JP) .............................. JP2019-036587

(51) Int. Cl.
*A61B 6/00* (2006.01)
*A61B 6/02* (2006.01)
*A61B 6/04* (2006.01)

(52) U.S. Cl.
CPC .............. *A61B 6/545* (2013.01); *A61B 6/025* (2013.01); *A61B 6/0414* (2013.01); *A61B 6/0435* (2013.01); *A61B 6/502* (2013.01); *A61B 6/5258* (2013.01)

(58) Field of Classification Search
CPC ........ A61B 6/025; A61B 6/0414; A61B 6/502
See application file for complete search history.

(56) References Cited

U.S. PATENT DOCUMENTS

| | | |
|---|---|---|
| 7,831,926 B2 | 11/2010 | Rohrabaugh et al. |
| 9,901,320 B2 | 2/2018 | DeFreitas et al. |
| 10,729,403 B2 | 8/2020 | DeFreitas et al. |
| 2003/0194050 A1 | 10/2003 | Eberhard et al. |
| 2014/0135623 A1 | 5/2014 | Manak et al. |
| 2017/0367671 A1 | 12/2017 | Arai et al. |
| 2017/0367674 A1 | 12/2017 | Arai et al. |
| 2017/0367675 A1 | 12/2017 | Arai et al. |

(Continued)

FOREIGN PATENT DOCUMENTS

| | | |
|---|---|---|
| JP | 2003325499 | 11/2003 |
| JP | 2014504918 | 2/2014 |
| JP | 2017099928 | 6/2017 |

(Continued)

OTHER PUBLICATIONS

"Office Action of Japan Counterpart Application" with English translation thereof, dated Dec. 14, 2021, p. 1-p. 5.

*Primary Examiner* — Dani Fox
(74) *Attorney, Agent, or Firm* — JCIPRNET

(57) ABSTRACT

A radiography system includes a mammography apparatus and a control device including a compression control unit that, in a case of performing continuous imaging in which the simple imaging and the tomosynthesis imaging are continuously performed while the breast being compressed by the mammography apparatus, performs control to cause a compression member to compress the breast at a first force in a first imaging of the simple imaging or the tomosynthesis imaging that is performed first in the continuous imaging, to change a force of the compression member compressing the breast from the first force to a second force lower than the first force after the first imaging, and to cause the compression member to compress the breast at the second force in a second imaging that is performed later.

29 Claims, 21 Drawing Sheets

(56) References Cited

U.S. PATENT DOCUMENTS

2020/0352543 A1  11/2020  DeFreitas et al.

FOREIGN PATENT DOCUMENTS

| | | |
|---|---|---|
| JP | 2017225633 | 12/2017 |
| JP | 2017225634 | 12/2017 |
| JP | 2017225635 | 12/2017 |
| WO | 2010028208 | 3/2010 |

RADIOGRAPHY SYSTEM, CONTROL METHOD, AND CONTROL PROGRAM

CROSS-REFERENCE TO RELATED APPLICATION

This application claims priority from Japanese Patent Application No. 2019-036587, filed Feb. 28, 2019, the disclosure of which is incorporated herein by reference in its entirety.

BACKGROUND

Technical Field

The present disclosure relates to a radiography system, a control method, and a non-transitory storage medium storing a control program.

Related Art

A mammography apparatus has been known which irradiates an object, such as the breast of a subject, with radiation emitted from a radiation source and detects the radiation transmitted through the object with a radiation detector to capture a radiographic image. In addition, simple imaging and tomosynthesis imaging have been known as the types of imaging performed by the mammography apparatus. The simple imaging means imaging that irradiates the breast with radiation R once to acquire one two-dimensional image. The tomosynthesis imaging means imaging that irradiates an object with radiation sequentially emitted from a radiation source at each of a plurality of different irradiation angles to acquire a projection image for each of the plurality of irradiation angles.

U.S. Pat. No. 7,831,296B discloses a mammography apparatus that performs the simple imaging and the tomosynthesis imaging for the breast in a compressed state as an object.

In general, the mammography apparatus captures a radiographic image in a state in which the breast is compressed by a compression member. Since the breast is pressed or stretched by being compressed by the compression member, the subject generally feels pain, which is a burden on the subject.

For this reason, JP2017-225633A discloses a technique that relieves the pain of the subject caused by the compression of the breast by a compression member.

However, there is a need for further relieving the pain of the subject caused by the compression of the breast by the compression member.

SUMMARY

The present disclosure has been made in view of the above-mentioned problems and an object of the present disclosure is to provide a radiography system, a control method, and a non-transitory storage medium storing a control program that may more effectively relieve the pain of a subject.

In order to achieve the object, according to a first aspect of the present disclosure, there is provided a radiography system comprising: a mammography apparatus that includes a radiation source, a radiation detector, and a compression member which compresses a breast disposed between the radiation source and the radiation detector and is capable of performing simple imaging that irradiates the breast in the compressed state with radiation emitted from the radiation source at a predetermined irradiation angle to capture a radiographic image and tomosynthesis imaging which sequentially irradiates the breast in the compressed state with the radiation emitted from the radiation source at each of a plurality of irradiation angles to capture a projection image for each of the plurality of irradiation angles; and a control device including a compression control unit that performs control to set a force of the compression member compressing the breast as a first force in one of the simple imaging and the tomosynthesis imaging which is performed first in continuous imaging in which the simple imaging and the tomosynthesis imaging are continuously performed for the breast compressed by the mammography apparatus, to change the force of the compression member compressing the breast from the first force to a second force lower than the first force after the one imaging, and to set the force of the compression member compressing the breast as the second force in the other of the simple imaging and the tomosynthesis imaging which is performed later.

According to a second aspect of the present disclosure, in the radiography system according to the first aspect, in a case in which the simple imaging is performed after the tomosynthesis imaging in the continuous imaging, the compression control unit may perform control to change the force of compressing the breast from the first force to the second force after the tomosynthesis imaging. In a case in which the tomosynthesis imaging is performed after the simple imaging in the continuous imaging, the compression control unit may perform control to change the force of compressing the breast from the first force to a third force higher than the first force after the simple imaging, instead of changing the force from the first force to the second force after the simple imaging, and to set the force of compressing the breast as the third force in the tomosynthesis imaging.

According to a third aspect of the present disclosure, in the radiography system according to the first aspect, in a case in which the simple imaging is performed after the tomosynthesis imaging in the continuous imaging, the compression control unit may perform control to change the force of compressing the breast from the first force to the second force after the tomosynthesis imaging. In a case in which the tomosynthesis imaging is performed after the simple imaging in the continuous imaging, the compression control unit may perform control to maintain the force of compressing the breast as the first force after the simple imaging, instead of changing the force of compressing the breast from the first force to the second force after the simple imaging.

According to a fourth aspect of the present disclosure, in the radiography system according to the first aspect, in a case in which the other imaging is the tomosynthesis imaging, the compression control unit may perform control to change the force of compressing the breast from the first force to the second force after the one imaging in a first tomosynthesis imaging mode. In a second tomosynthesis imaging mode having a wider irradiation angle range than the first tomosynthesis imaging mode, the compression control unit may perform control to maintain the force of compressing the breast as the first force after the simple imaging, instead of changing the force of compressing the breast from the first force to the second force after the simple imaging.

According to a fifth aspect of the present disclosure, in the radiography system according to the first aspect, the compression control unit may perform control to maintain the force of compressing the breast as the first force after the one imaging on the basis of at least one of the radiographic image or the projection image captured by the mammography apparatus, instead of changing the force of compressing the breast from the first force to the second force after the one imaging.

According to a sixth aspect of the present disclosure, in the radiography system according to the fifth aspect, in a case in which it is estimated that an artifact is not included in the breast on the basis of the one image, the compression control unit may perform control to change the force of compressing the breast from the first force to the second force after the one imaging. In a case in which it is estimated that the artifact is included in the breast, the compression control unit may perform control to maintain the force of compressing the breast as the first force after the one imaging, instead of changing the force of compressing the breast from the first force to the second force after the one imaging.

According to a seventh aspect of the present disclosure, in the radiography system according to any one of the first to sixth aspects, in a case in which the radiation source is moved after the one imaging and before the other imaging, a movement period of the radiation source and a change period for which the force of compressing the breast is changed after the one imaging ends may overlap each other.

According to an eighth aspect of the present disclosure, in the radiography system according to any one of the first to seventh aspects, the mammography apparatus may further comprise: a grid that removes a scattered ray; and a grid moving unit that moves the grid to a first position between the radiation source and the radiation detector in the simple imaging and moves the grid to a second position which is different from the first position and is retracted from the radiation detector as viewed from the radiation source in the tomosynthesis imaging. In the continuous imaging, a movement period for which the grid moving unit moves the grid from one of the first position and the second position to the other and a change period for which the force of compressing the breast is changed after the one imaging ends may overlap each other.

According to a ninth aspect of the present disclosure, in the radiography system according to the eighth aspect, in a case in which the tomosynthesis imaging is performed after the simple imaging in the continuous imaging, a movement period for which the grid moving unit moves the grid from the first position to the second position and the change period for which the force of compressing the breast is changed after the one imaging ends may overlap each other.

According to a tenth aspect of the present disclosure, in the radiography system according to the eighth or ninth aspect, in a case in which the simple imaging is performed after the tomosynthesis imaging in the continuous imaging, a movement period for which the grid moving unit moves the grid from the second position to the first position and the change period for which the force of compressing the breast is changed after the one imaging ends may overlap each other.

According to an eleventh aspect of the present disclosure, in the radiography system according to any one of the first to tenth aspects, the compression control unit may perform control such that the compression member is moved in a decompression direction to change the force from the first force to the second force.

According to a twelfth aspect of the present disclosure, in the radiography system according to any one of the first to eleventh aspects, the force of compressing the breast may be a compression force of compressing the entire breast, the first force may be a first compression force, and the second force may be a second compression force.

According to a thirteenth aspect of the present disclosure, in the radiography system according to any one of the first to eleventh aspects, the force of compressing the breast may be a compression pressure which is a compression force per unit area, the first force may be a first compression pressure, and the second force may be a second compression pressure.

According to achieve the object, according to a fourteenth aspect of the present disclosure, there is provided a control method comprising: in continuous imaging in which a mammography apparatus that includes a radiation source, a radiation detector, and a compression member which compresses a breast disposed between the radiation source and the radiation detector and is capable of performing simple imaging that irradiates the breast in the compressed state with radiation emitted from the radiation source at a predetermined irradiation angle to capture a radiographic image and tomosynthesis imaging which sequentially irradiates the breast in the compressed state with the radiation emitted from the radiation source at each of a plurality of irradiation angles to capture a projection image for each of the plurality of irradiation angles continuously performs the simple imaging and the tomosynthesis imaging for the breast in the compressed state, performing control to set a force of the compression member compressing the breast as a first force in one of the simple imaging and the tomosynthesis imaging which is performed first, to change the force of the compression member compressing the breast from the first force to a second force lower than the first force after the one imaging, and to set the force of the compression member compressing the breast as the second force in the other of the simple imaging and the tomosynthesis imaging which is performed later.

According to a fifteenth aspect of the present disclosure, in the control method according to the fourteenth aspect, in a case in which the simple imaging is performed after the tomosynthesis imaging in the continuous imaging, control may be performed to change the force of compressing the breast from the first force to the second force after the tomosynthesis imaging. In a case in which the tomosynthesis imaging is performed after the simple imaging in the continuous imaging, control may be performed to change the force of compressing the breast from the first force to a third force higher than the first force after the simple imaging, instead of changing the force from the first force to the second force after the simple imaging, and to set the force of compressing the breast as the third force in the tomosynthesis imaging.

According to a sixteenth aspect of the present disclosure, in the control method according to the fourteenth aspect, in a case in which the simple imaging is performed after the tomosynthesis imaging in the continuous imaging, control may be performed to change the force of compressing the breast from the first force to the second force after the tomosynthesis imaging. In a case in which the tomosynthesis imaging is performed after the simple imaging in the continuous imaging, control may be performed to maintain the force of compressing the breast as the first force after the simple imaging, instead of changing the force from the first force to the second force after the simple imaging.

According to a seventeenth aspect of the present disclosure, in the control method according to the fourteenth aspect, in a case in which the other imaging is the tomosynthesis imaging, control may be performed to change the force of compressing the breast from the first force to the second force after the one imaging in a first tomosynthesis imaging mode. In a second tomosynthesis imaging mode having a wider irradiation angle range than the first tomosynthesis imaging mode, control may be performed to maintain the force of compressing the breast as the first force after the simple imaging, instead of changing the force of compressing the breast from the first force to the second force after the simple imaging.

According to an eighteenth aspect of the present disclosure, in the control method according to the fourteenth aspect, control may be performed to maintain the force of compressing the breast as the first force after the one imaging, instead of changing the force of compressing the breast from the first force to the second force after the one imaging, on the basis of at least one of the radiographic image or the projection image captured by the mammography apparatus.

According to a nineteenth aspect of the present disclosure, in the control method according to the eighteenth aspect, in a case in which it is estimated that an artifact is not included in the breast on the basis of the one image, control may be performed to change the force of compressing the breast from the first force to the second force after the one imaging. In a case in which it is estimated that the artifact is included in the breast, control may be performed to maintain the force of compressing the breast as the first force after the one imaging, instead of changing the force of compressing the breast from the first force to the second force after the one imaging.

According to a twentieth aspect of the present disclosure, in the control method according to any one of the fourteenth to nineteenth aspects, in a case in which the radiation source is moved after the one imaging and before the other imaging, a movement period of the radiation source and a change period for which the force of compressing the breast is changed after the one imaging ends may overlap each other.

According to a twenty-first aspect of the present disclosure, the control method according to any one of the fourteenth to twentieth aspects may further comprise: moving a grid that is provided in the mammography apparatus and removes a scattered ray to a first position between the radiation source and the radiation detector in the simple imaging; and moving the grid to a second position which is different from the first position and is retracted from the radiation detector as viewed from the radiation source in the tomosynthesis imaging. In the continuous imaging, a movement period for which the grid is moved from one of the first position and the second position to the other and a change period for which the force of compressing the breast is changed after the one imaging ends may overlap each other.

According to a twenty-second aspect of the present disclosure, in the control method according to the twenty-first aspect, in a case in which the tomosynthesis imaging is performed after the simple imaging in the continuous imaging, a movement period for which the grid is moved from the first position to the second position and the change period for which the force of compressing the breast is changed after the one imaging ends may overlap each other.

According to a twenty-third aspect of the present disclosure, in the control method according to the twenty-first or twenty-second aspect, in a case in which the simple imaging is performed after the tomosynthesis imaging in the continuous imaging, a movement period for which the grid is moved from the second position to the first position and the change period for which the force of compressing the breast is changed after the one imaging ends may overlap each other.

According to a twenty-fourth aspect of the present disclosure, in the control method according to any one of the fourteenth or twenty-third aspects, control may be performed such that the compression member is moved in a decompression direction to change the force from the first force to the second force.

According to a twenty-fifth aspect of the present disclosure, in the control method according to any one of the fourteenth or twenty-fourth aspects, the force of compressing the breast may be a compression force of compressing the entire breast, the first force may be a first compression force, and the second force may be a second compression force.

According to a twenty-sixth aspect of the present disclosure, in the control method according to any one of the fourteenth or twenty-fourth aspects, the force of compressing the breast may be a compression pressure which is a compression force per unit area, the first force may be a first compression pressure, and the second force may be a second compression pressure.

In order to achieve the object, according to a twenty-seventh aspect of the present disclosure, there is provided a control program that causes a computer to perform: in continuous imaging in which a mammography apparatus that includes a radiation source, a radiation detector, and a compression member which compresses a breast disposed between the radiation source and the radiation detector and is capable of performing simple imaging that irradiates the breast in the compressed state with radiation emitted from the radiation source at a predetermined irradiation angle to capture a radiographic image and tomosynthesis imaging which sequentially irradiates the breast in the compressed state with the radiation emitted from the radiation source at each of a plurality of irradiation angles to capture a projection image for each of the plurality of irradiation angles continuously performs the simple imaging and the tomosynthesis imaging for the breast in the compressed state, performing control to set a force of the compression member compressing the breast as a first force in one of the simple imaging and the tomosynthesis imaging which is performed first, to change the force of the compression member compressing the breast from the first force to a second force lower than the first force after the one imaging, and to set the force of the compression member compressing the breast as the second force in the other of the simple imaging and the tomosynthesis imaging which is performed later.

A control device according to the present disclosure includes a processor. In a case in which a mammography apparatus that includes a radiation source, a radiation detector, and a compression member which compresses a breast disposed between the radiation source and the radiation detector and is capable of performing simple imaging that irradiates the breast in the compressed state with radiation emitted from the radiation source at a predetermined irradiation angle to capture a radiographic image and tomosynthesis imaging which sequentially irradiates the breast in the compressed state with the radiation emitted from the radiation source at each of a plurality of irradiation angles to capture a projection image for each of the plurality of irradiation angles continuously performs the simple imaging and the tomosynthesis imaging for the breast in the compressed state, the process performs control to set a force of the compression member compressing the breast as a first force in one of the simple imaging and the tomosynthesis imaging which is performed first, to change the force of the compression member compressing the breast from the first force to a second force lower than the first force after the one imaging, and to set the force of the compression member compressing the breast as the second force in the other of the simple imaging and the tomosynthesis imaging which is performed later.

According to the present disclosure, it is possible to more effectively relieve the pain of the subject.

DETAILED DESCRIPTION

Hereinafter, embodiments of the invention will be described in detail with reference to the drawings. Each of the embodiments does not limit the invention. In each of the embodiments, for example, a case in which an object of interest of the present disclosure is the mammary gland will be described.

First Embodiment

In this embodiment, an aspect in which a compression force of compressing the entire breast is an example of the force of compressing the breast according to the present disclosure will be described.

Figure 1:
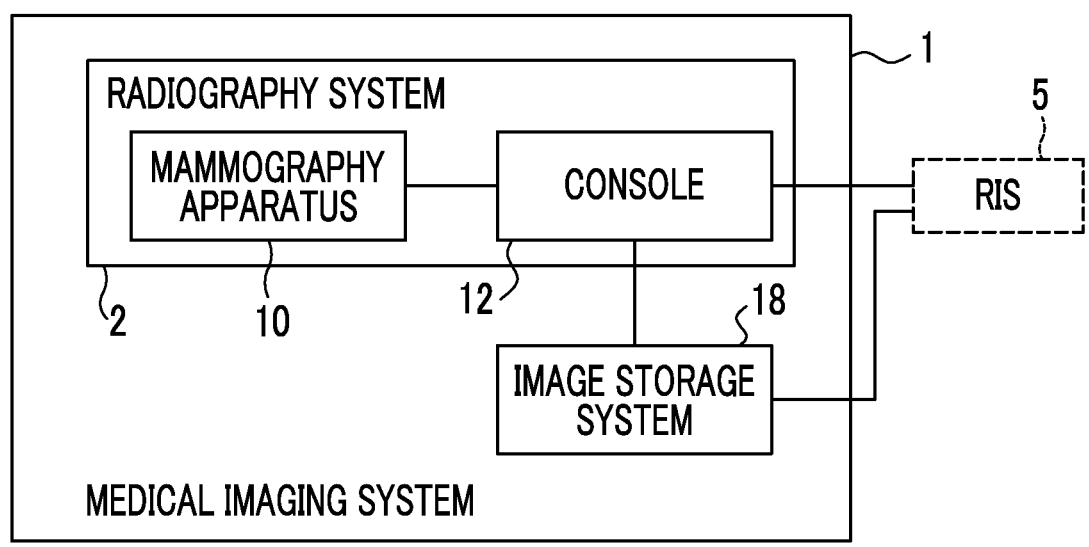
FIG. 1 is a diagram schematically illustrating an example of the overall configuration of a medical imaging system according to a first embodiment.

First, an example of the overall configuration of a medical imaging system according to this embodiment will be described. FIG. 1 is a diagram illustrating an example of the overall configuration of a medical imaging system 1 according to this embodiment.

As illustrated in FIG. 1, the medical imaging system 1 according to this embodiment comprises a radiography system 2, and an image storage system 18.

Figure 2:
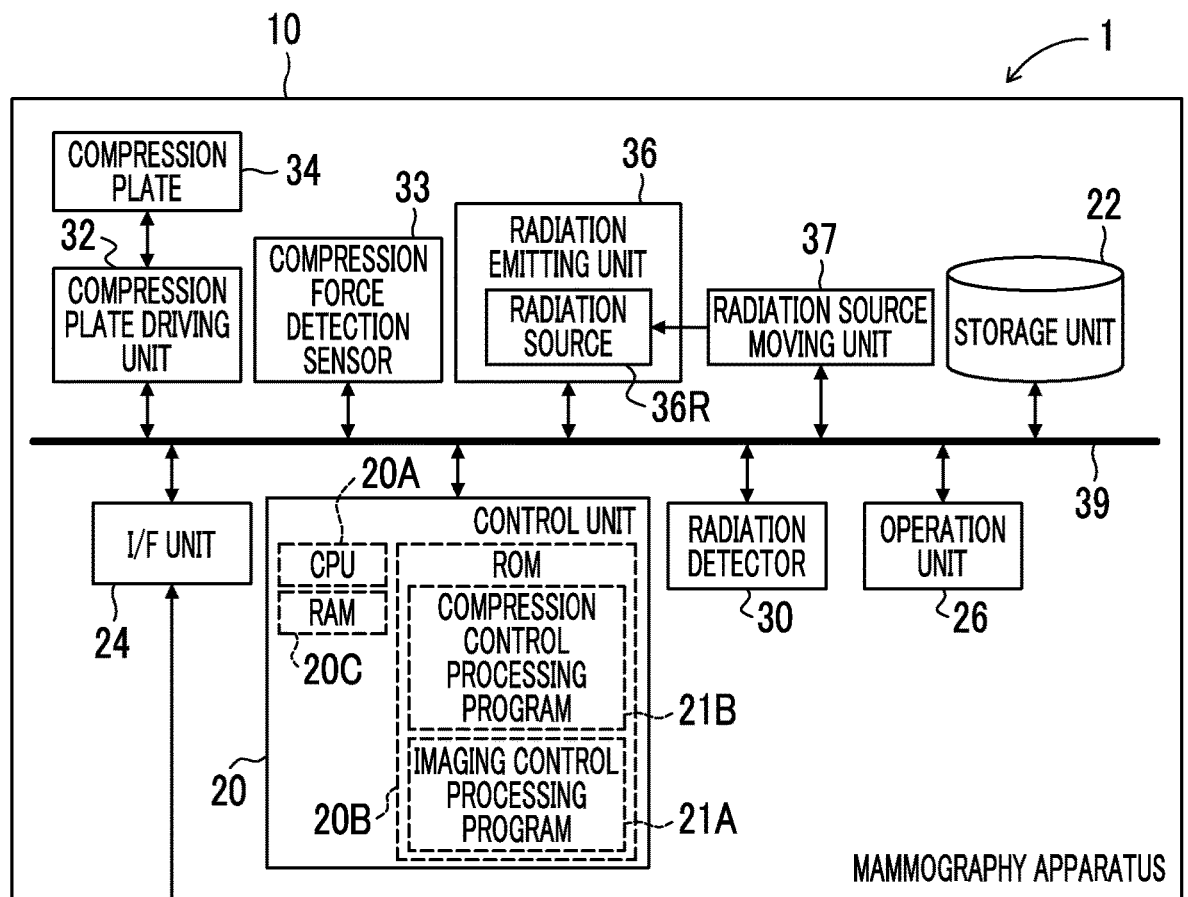
FIG. 2 is a block diagram illustrating an example of the configuration of a console and a mammography apparatus according to the first embodiment.
Figure 3:
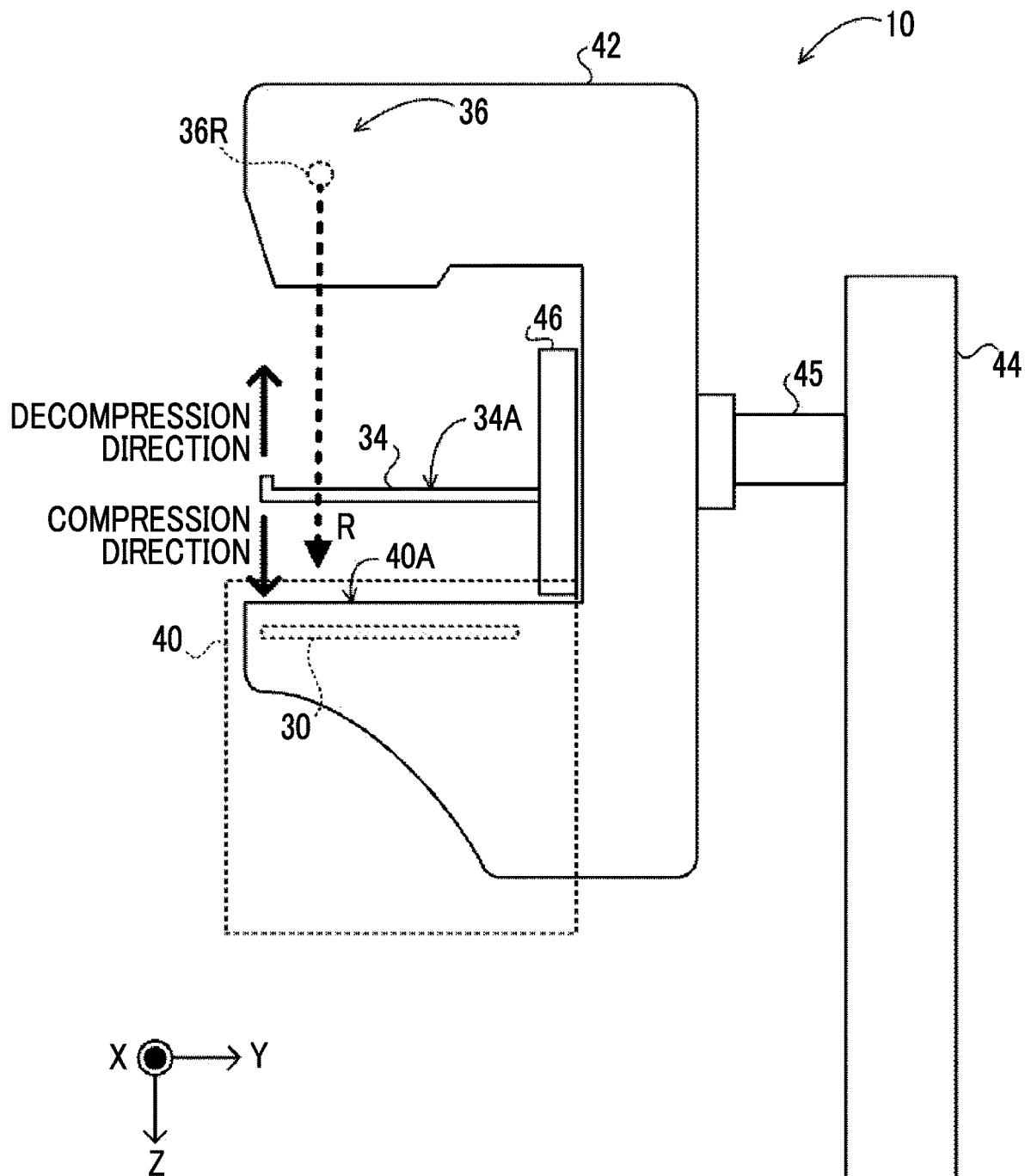
FIG. 3 is a side view illustrating an example of the outward appearance of the mammography apparatus according to the first embodiment.

First, the configuration of the radiography system 2 will be described. The radiography system 2 includes a mammography apparatus 10 and a console 12. FIG. 2 is a block diagram illustrating an example of the configuration of the mammography apparatus 10 and the console 12. FIG. 3 is a side view illustrating an example of the outward appearance of the mammography apparatus 10 according to this embodiment.

The mammography apparatus 10 according to this embodiment irradiates the breast of a subject as an object with radiation R (for example, X-rays) to capture a radiographic image of the breast. In addition, the mammography apparatus 10 may be an apparatus that captures the image of the breast of the subject not only in a state in which the subject stands up (standing state) but also in a state in which the subject sits on, for example, a chair (including a wheelchair) (sitting state).

As illustrated in FIG. 2, the mammography apparatus 10 according to this embodiment comprises a control unit 20, a storage unit 22, an interface (I/F) unit 24, an operation unit 26, a radiation detector 30, a compression plate driving unit 32, a compression force detection sensor 33, a compression plate 34, a radiation emitting unit 36, and a radiation source moving unit 37. The control unit 20, the storage unit 22, the I/F unit 24, the operation unit 26, the radiation detector 30, the compression plate driving unit 32, the compression force detection sensor 33, the radiation emitting unit 36, and the radiation source moving unit 37 are connected to each other through a bus 39, such as a system bus or a control bus, such that they can transmit and receive various kinds of information.

The control unit 20 according to this embodiment controls the overall operation of the mammography apparatus 10 under the control of the console 12. The control unit 20 comprises a central processing unit (CPU) 20A, a read only memory (ROM) 20B, and a random access memory (RAM) 20C. For example, various programs including an imaging processing program 21A and a compression control processing program 21B which are executed by the CPU 20A and perform control related to the capture of a radiographic image are stored in the ROM 20B in advance. The RAM 20C temporarily stores various kinds of data. The compression control processing program 21B according to this embodiment is an example of a control program according to the present disclosure.

The radiation detector 30 detects the radiation R transmitted through the breast which is the object. As illustrated in FIG. 3, the radiation detector 30 is provided in an imaging table 40. In the mammography apparatus 10 according to this embodiment, in a case in which imaging is performed, the breast of the subject is positioned on an imaging surface 40A of the imaging table 40 by a user such as a doctor or a radiology technician. For example, the imaging surface 40A with which the breast of the subject comes into contact is made of carbon in terms of the transmission and intensity of the radiation R.

The radiation detector 30 detects the radiation R transmitted through the breast of the subject and the imaging table 40, generates a radiographic image on the basis of the detected radiation R, and outputs image data indicating the generated radiographic image. The type of the radiation detector 30 according to this embodiment is not particularly limited. For example, the radiation detector 30 may be an indirect-conversion-type radiation detector that converts the radiation R into light and converts the converted light into charge or a direct-conversion-type radiation detector that directly converts the radiation R into charge.

For example, the image data of the radiographic image captured by the radiation detector 30 and various other kinds of information are stored in the storage unit 22. Examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 30 in the mammography apparatus 10 is transmitted to the console 12 through the I/F unit 24 by wireless communication or wired communication.

The operation unit 26 is provided as a plurality of switches in, for example, the imaging table 40 of the mammography apparatus 10. In addition, the operation unit 26 may be provided as a touch panel switch or may be provided as a foot switch that is operated by the user's feet.

The radiation emitting unit 36 comprises a radiation source 36R. As illustrated in FIG. 3, the radiation emitting unit 36 is provided in an arm portion 42 together with the imaging table 40 and a compression unit 46. In addition, as illustrated in FIG. 3, the mammography apparatus 10 according to this embodiment comprises the arm portion 42, a base 44, and a shaft portion 45. The arm portion 42 is supported by the base 44 so as to be movable in the up-down direction (Z-axis direction). The shaft portion 45 connects the arm portion 42 to the base 44. The radiation source moving unit 37 can relatively rotate the arm portion 42 with respect to the base 44, using the shaft portion 45 as a rotation axis.

Figure 4:
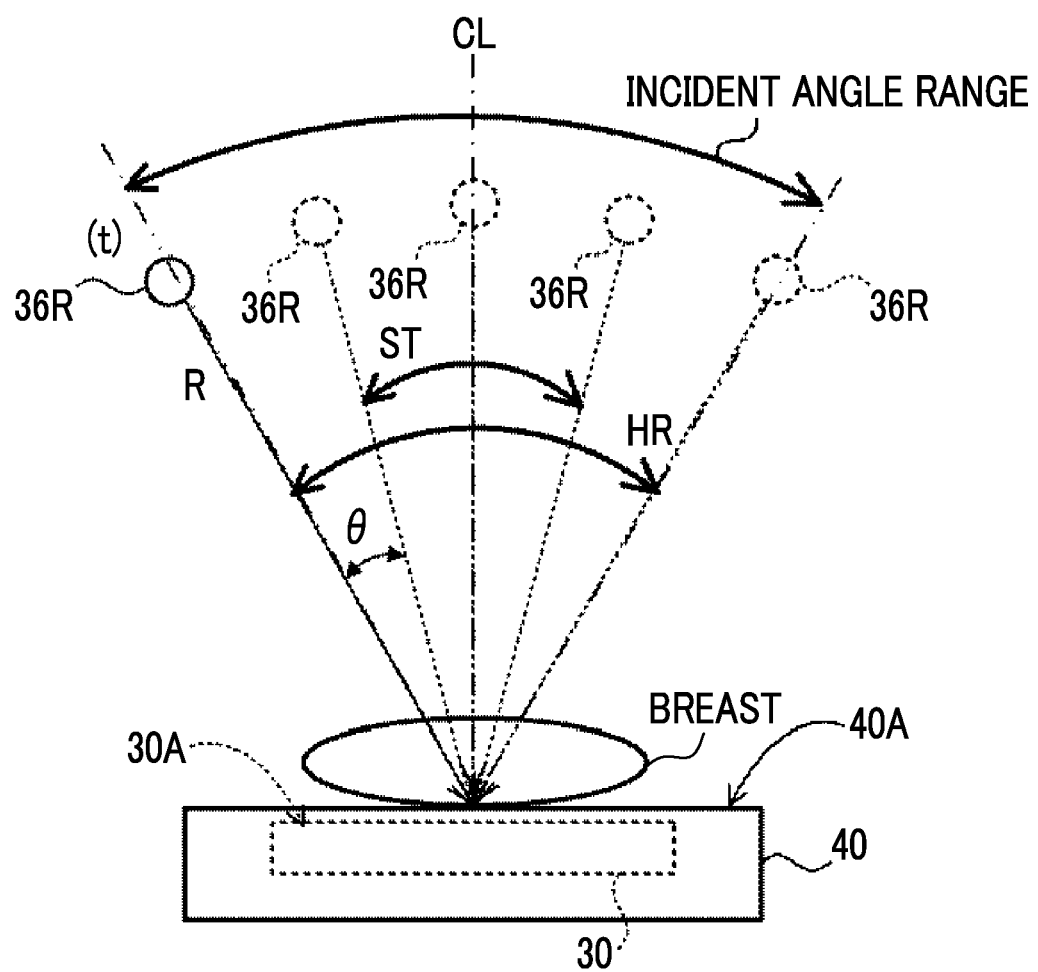
FIG. 4 is a diagram illustrating tomosynthesis imaging performed by the mammography apparatus according to the first embodiment.

In a case in which the mammography apparatus 10 performs tomosynthesis imaging, with the rotation of the arm portion 42, the radiation source 36R of the radiation emitting unit 36 is continuously moved to each of a plurality of irradiation positions with different irradiation angles by the radiation source moving unit 37. In this embodiment, as illustrated in FIG. 4, the radiation source 36R is moved to the irradiation positions t (t=0, 1, ..., T; in FIG. 4, T=5) with different irradiation angles which are arranged at an interval of a predetermined angle θ, that is, the positions where the radiation R is incident on a detection surface 30A of the radiation detector 30 at different angles. At each irradiation position, the radiation R is emitted from the radiation source 36R in response to a command from the console 12 and the radiation detector 30 captures a radiographic image. Hereinafter, the radiographic image captured by the radiation detector 30 at each of the plurality of irradiation positions t with different irradiation angles in tomosynthesis imaging is referred to as a "projection image". In a case in which the radiography system 2 performs tomosynthesis imaging that moves the radiation source 36R to each irradiation position t and captures a projection image at each irradiation position t, T projection images are obtained.

Hereinafter, as illustrated in FIG. 4, the range of the irradiation angle in the tomosynthesis imaging is referred to as an "irradiation angle range". In a case in which the mammography apparatus 10 according to this embodiment performs the tomosynthesis imaging, there are two modes, that is, a standard (ST) mode and a high resolution (HR) mode. As illustrated in FIG. 4, an irradiation angle range HR in the high resolution mode is wider than an irradiation angle range ST in the standard mode. For example, in the mammography apparatus 10 according to this embodiment, the number of irradiation positions t, that is, the number of projection images captured is the same in the standard mode and the high resolution mode. Therefore, in the standard mode, the difference between the irradiation angles at each irradiation position t is small and the imaging time is shorter than that in the high resolution mode. On the other hand, in the high resolution mode, the difference between the irradiation angles at each irradiation position t is large and resolution in the depth direction is higher than that in the standard mode. The standard mode is an example of a first tomosynthesis imaging mode according to the present disclosure and the high resolution mode is an example of a second tomosynthesis imaging mode according to the present disclosure.

In contrast, in a case in which the mammography apparatus 10 performs simple imaging, the radiation source 36R of the radiation emitting unit 36 is located at the irradiation position t (an irradiation angle of 0 degrees) along a normal line CL to the radiation detector 30. The "simple imaging" means imaging that irradiates the breast with the radiation R once to acquire one two-dimensional image. Hereinafter, the radiographic image captured by the radiation detector 30 in the simple imaging is referred to as a "two-dimensional image". In a case in which the projection image and the two-dimensional image are generically referred to without being distinguished from each other, they are simply referred to as "radiographic images".

Figure 5:
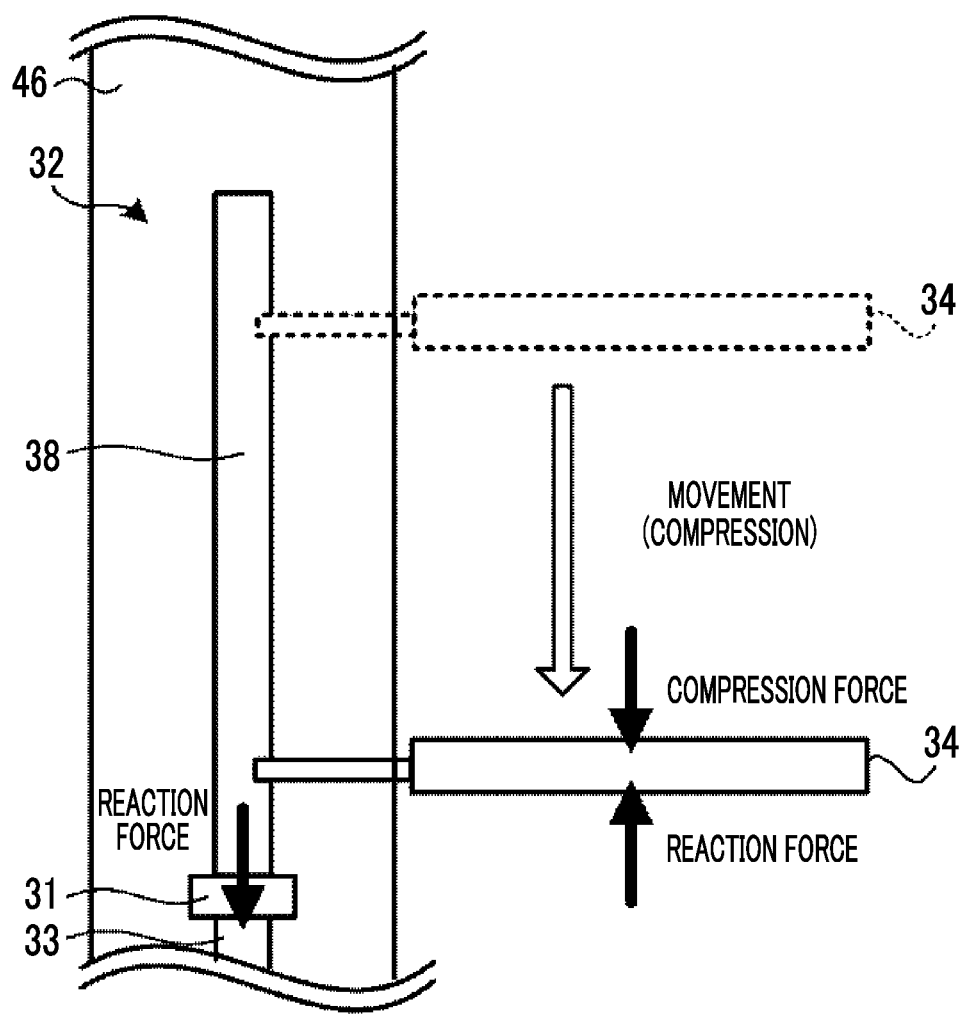
FIG. 5 is a diagram illustrating an example of a configuration in a case in which a compression force is detected by load applied to a motor in the first embodiment.

As illustrated in FIGS. 3 and 5, the compression plate driving unit 32, the compression force detection sensor 33, and the compression plate 34 are provided in the compression unit 46. Each of the compression unit 46 and the arm portion 42 can be relatively rotated with respect to the base 44, using the shaft portion 45 as a rotation axis. In this embodiment, gears (not illustrated) are provided in each of the shaft portion 45, the arm portion 42, and the compression unit 46. Each gear is switched between an engaged state and a disengaged state to connect each of the arm portion 42 and the compression unit 46 to the shaft portion 45. One or both of the arm portion 42 and the compression unit 46 connected to the shaft portion 45 are rotated integrally with the shaft portion 45.

The compression plate 34 according to this embodiment is a plate-shaped compression member and is moved in the up-down direction (Z-axis direction) by the compression plate driving unit 32 to compress the breast of the subject against the imaging table 40. As illustrated in FIG. 3, for the movement direction of the compression plate 34, the direction in which the breast is compressed, that is, the direction in which the compression plate 34 becomes closer to the imaging surface 40A is referred to as a "compression direction" and the direction in which the compression of the breast is released, that is, the direction in which the compression plate 34 becomes closer to the radiation emitting unit 36 is referred to as a "decompression direction".

As illustrated in FIG. 5, the compression unit 46 comprises the compression plate driving unit 32 including a motor 31 and a ball screw 38 and the compression force detection sensor 33. The compression force detection sensor 33 has a function of detecting the compression force of the compression plate 34 against the entire breast. In the example illustrated in FIG. 5, the compression force detection sensor 33 detects the compression force on the basis of the load applied to the motor 31 as a driving source of the compression plate 34. The compression plate 34 is supported by the ball screw 38 and the motor 31 is driven to slide the compression plate 34 between the imaging table 40 and the radiation source 36R. The compression force detection sensor 33 according to this embodiment is a strain gauge, such as a load cell. The compression force detection sensor 33 detects reaction force to the compression force of the compression plate 34 to detect the compression force of the compression plate 34 against the breast.

A method for detecting the compression force is not limited thereto. For example, the compression force detection sensor 33 may be a semiconductor pressure sensor or a capacitive pressure sensor. Further, for example, the compression force detection sensor 33 may be provided in the compression plate 34.

It is preferable that the compression plate 34 is optically transparent in order to check positioning or a compressed state in the compression of the breast. In addition, the compression plate 34 is made of a material having high transmittance for the radiation R. Examples of the material forming the compression plate 34 include resins such as polymethylpentene, polycarbonate, acrylic, and polyethylene terephthalate. The member forming the compression plate 34 is not limited to this embodiment. For example, the member forming the compression plate 34 may be a film-like member. The compression plate 34 according to this embodiment is an example of a compression member according to the present disclosure.

Figure 6:
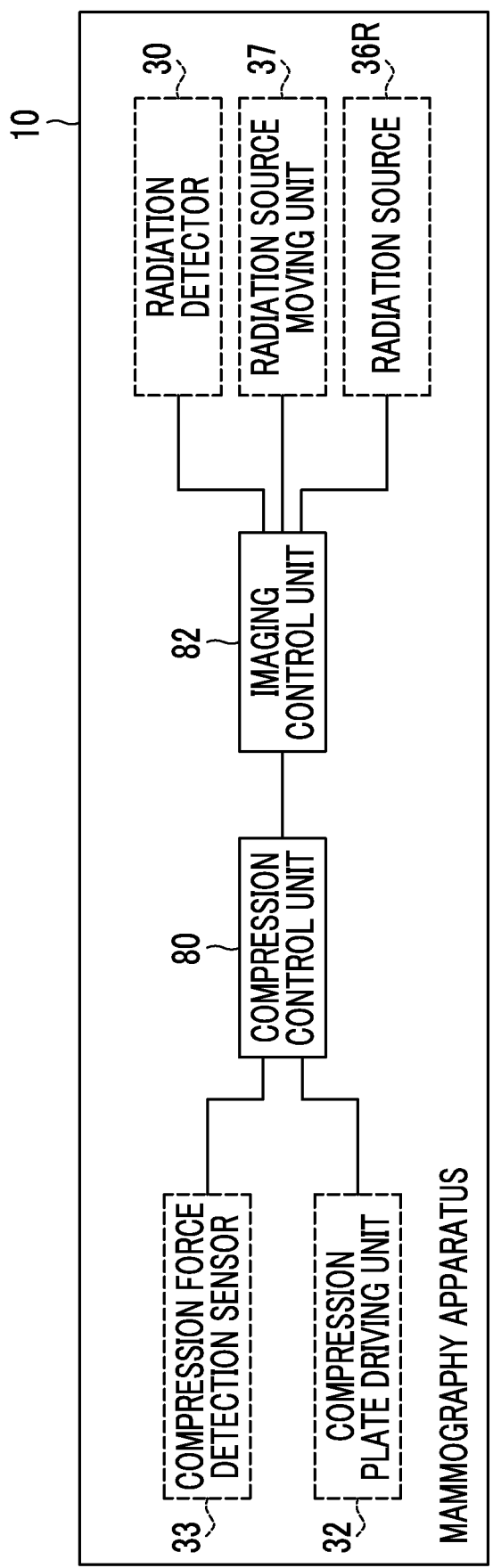
FIG. 6 is a functional block diagram illustrating an example of the function of the mammography apparatus according to the first embodiment.

FIG. 6 is a functional block diagram illustrating an example of the configuration of the mammography apparatus 10 according to this embodiment. As illustrated in FIG. 6, the mammography apparatus 10 according to this embodiment comprises a compression control unit 80 and an imaging control unit 82. For example, in the mammography apparatus 10 according to this embodiment, the CPU 20A of the control unit 20 executes the compression control processing program 21B stored in the ROM 20B such that the control unit 20 functions as the compression control unit 80. The mammography apparatus 10 according to this embodiment is an example of a control device according to the present disclosure. For example, in the mammography apparatus 10 according to this embodiment, the CPU 20A of the control unit 20 executes the imaging processing program 21A stored in the ROM 20B such that the control unit 20 functions as the imaging control unit 82.

The radiation detector 30, the radiation source moving unit 37, and the radiation source 36R are connected to the imaging control unit 82 of the mammography apparatus 10. The imaging control unit 82 controls the capture of a radiographic image by the radiation detector 30, the movement of the radiation source 36R (radiation emitting unit 36) by the radiation source moving unit 37, and the emission of the radiation R from the radiation source 36R.

Information indicating the compression force which is the detection result of the compression force detection sensor 33 is input to the compression control unit 80 of the mammography apparatus 10. The compression control unit 80 outputs a command related to the movement of the compression plate 34 to the compression plate driving unit 32.

In the case of continuous imaging that continuously performs the simple imaging and the tomosynthesis imaging in a state in which the mammography apparatus 10 compresses the breast, the compression control unit 80 performs control to set the compression force of the compression plate 34 against the breast as a first compression force in one of the simple imaging and the tomosynthesis imaging which is performed first. In addition, the compression control unit 80 performs control to change the compression force of the compression plate 34 from the first compression force to a second compression force lower than the first compression force after the one imaging and performs control to set the compression force of the compression plate 34 against the breast as the second compression force in the other of the simple imaging and the tomosynthesis imaging which is performed later.

In some cases, the mammography apparatus 10 according to this embodiment performs the continuous imaging in a state in which the breast is compressed by the compression plate 34. In the case of the continuous imaging, the imaging time for which the breast is continuously compressed by the compression plate 34 is long. Therefore, the compression control unit 80 sets the compression force in one of the tomosynthesis imaging and the simple imaging which is performed later to be lower than the compression force in the other of the tomosynthesis imaging and the simple imaging which is performed first such that the pain of the subject caused by the compression of the breast is relieved.

The console 12 according to this embodiment has a function of controlling the mammography apparatus 10 using, for example, an imaging order and various kinds of information acquired from a radiology information system (RIS) 5 through a wireless communication local area network (LAN) and commands input by the user through an operation unit 56.

For example, the console 12 according to this embodiment is a server computer. As illustrated in FIG. 2, the console 12 comprises a control unit 50, a storage unit 52, an I/F unit 54, the operation unit 56, and a display unit 58. The control unit 50, the storage unit 52, the I/F unit 54, operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including a control processing program 51 (which will be described below) executed by the CPU 50A are stored in the ROM 50B in advance. The RAM 50C temporarily stores various kinds of data.

For example, the image data of the radiographic image captured by the mammography apparatus 10 and various other kinds of information are stored in the storage unit 52. An HDD or an SSD is given as an example of the storage unit 52.

The operation unit 56 is used by the user to input, for example, commands which are related to the capture of a radiographic image and include a command to emit the radiation R or various kinds of information. Therefore, the operation unit 56 according to this embodiment includes at least an irradiation command button that is pressed by the user to input a command to emit the radiation R. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information to and from the mammography apparatus 10, the RIS 5, and the image storage system 18 using wireless communication or wired communication. In the radiography system 2 according to this embodiment, the console 12 receives the image data of the radiographic image captured by the mammography apparatus 10 from the mammography apparatus 10 through the I/F unit 54, using wireless communication or wired communication.

Figure 7:
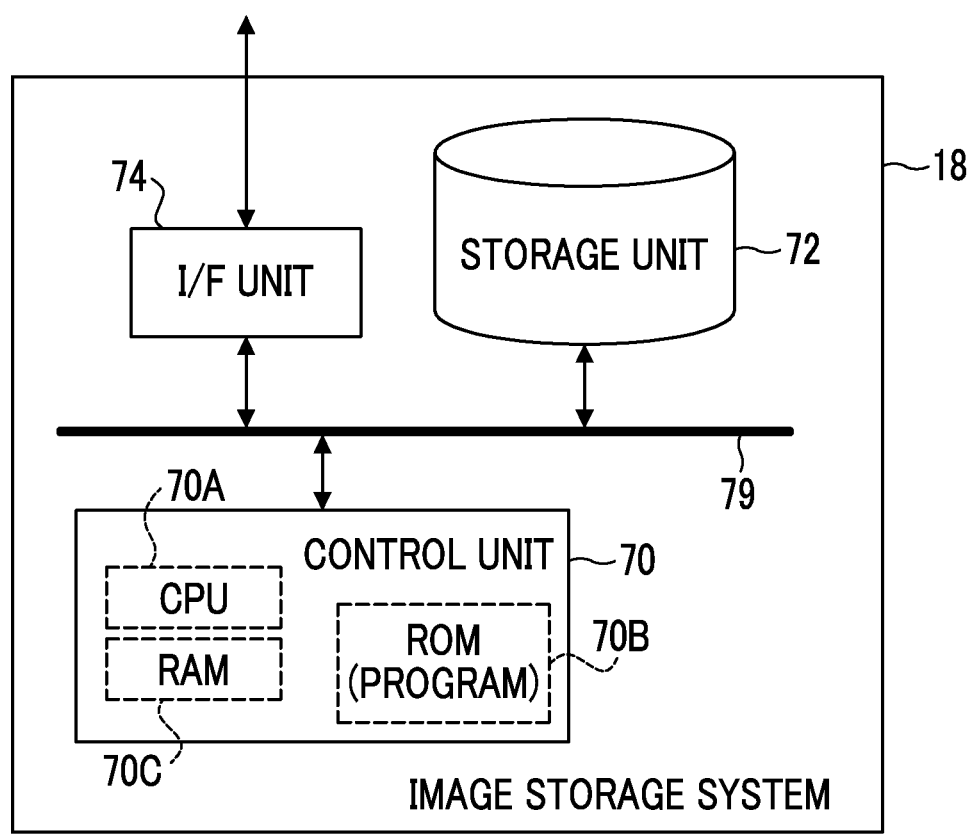
FIG. 7 is a block diagram illustrating an example of the configuration of an image storage system according to the first embodiment.

Next, the configuration of the image storage system 18 will be described. FIG. 7 is a block diagram illustrating an example of the configuration of the image storage system 18. The image storage system 18 stores the image data of the radiographic image captured by the radiography system 2. The image storage system 18 extracts an image corresponding to a request from, for example, the console 12 and other reading devices (not illustrated) from the stored radiographic images and transmits the extracted image to the apparatus which is the request source. A specific example of the image storage system 18 is a picture archiving and communication system (PACS).

As illustrated in FIG. 7, the image storage system 18 comprises a control unit 70, a storage unit 72, and an I/F unit 74. The control unit 70, the storage unit 72, and the I/F unit 74 are connected to each other through a bus 79, such as a system bus or a control bus, such that they can transmit and receive various kinds of information.

The control unit 70 according to this embodiment controls the overall operation of the image storage system 18. The control unit 70 comprises a CPU 70A, a ROM 70B, and a RAM 70C. For example, various programs executed by the CPU 70A are stored in the ROM 70B in advance. The RAM 70C temporarily stores various kinds of data.

The storage unit 72 is a so-called database that stores each of the image data of the radiographic image and the image data of the ultrasound image so as to be associated with, for example, an imaging order or information released to the subject.

The I/F unit 74 has a function of transmitting and receiving various kinds of information to and from the console 12 using wireless communication or wired communication.

Next, the operation of the mammography apparatus 10 according to this embodiment will be described with reference to the drawings.

Figure 8:
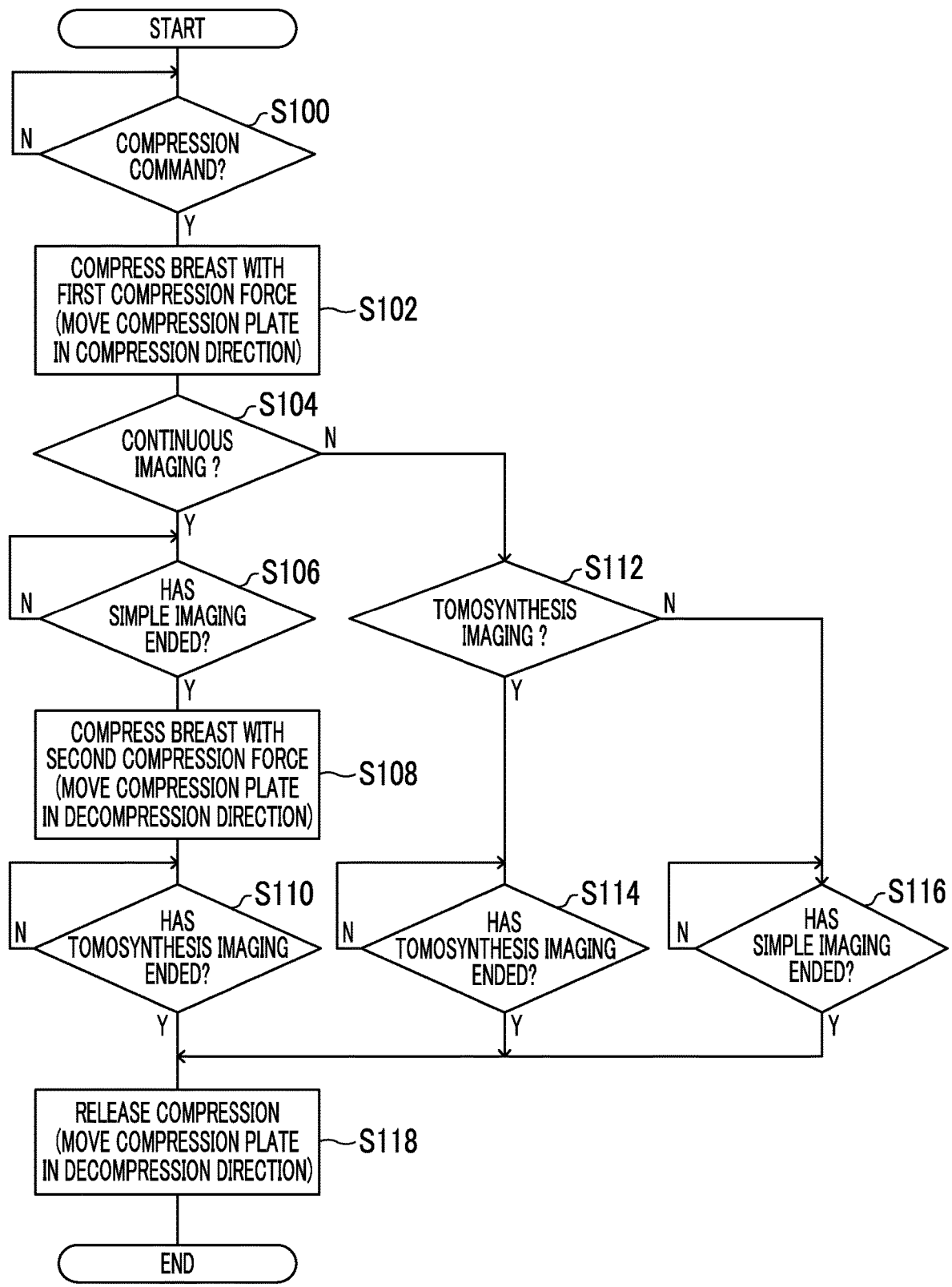
FIG. 8 is a flowchart illustrating an example of the flow of a compression control process of the mammography apparatus according to the first embodiment.
Figure 9:
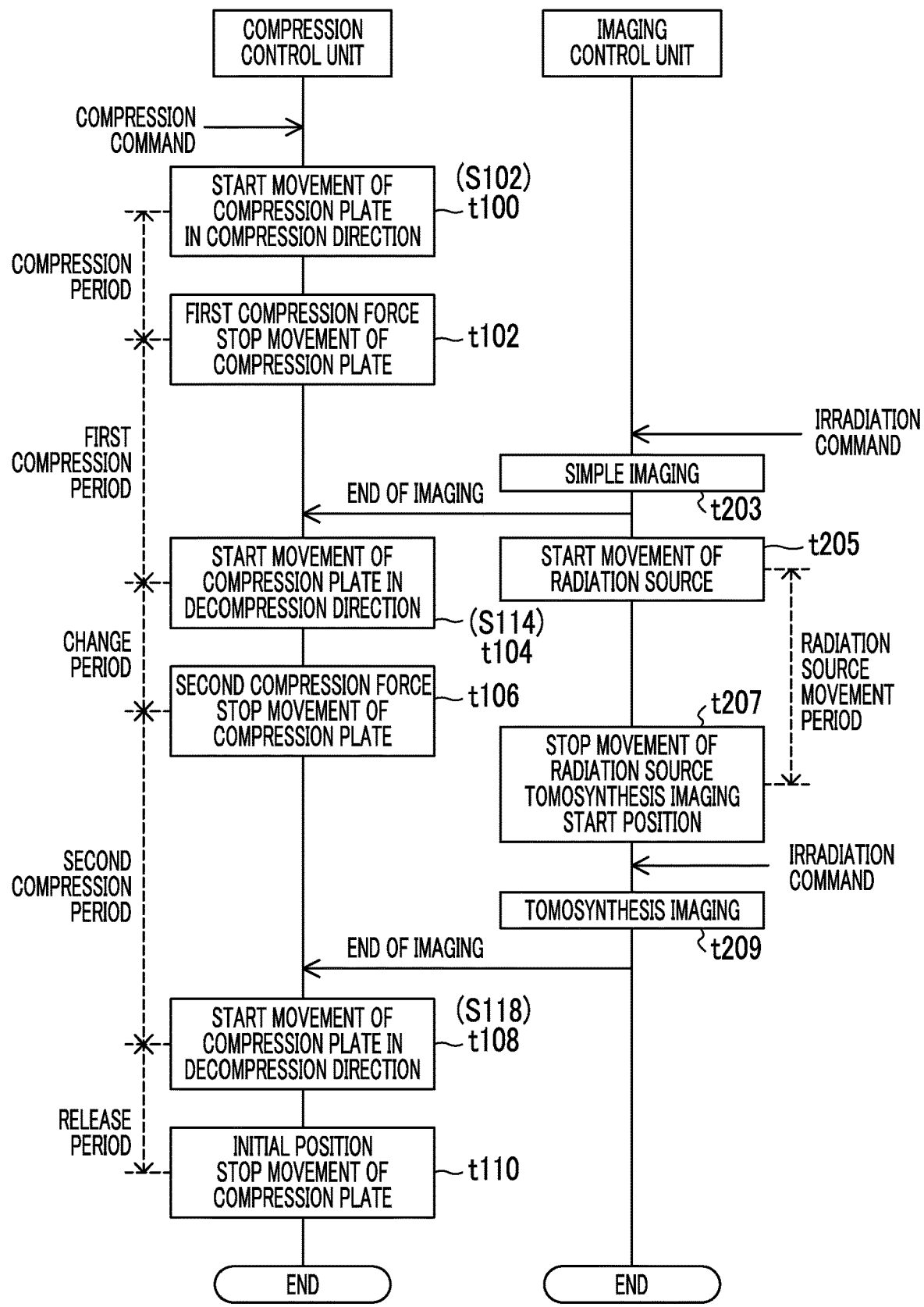
FIG. 9 is a timing chart illustrating an example of the operation of a compression control unit and an imaging control unit in a case in which the mammography apparatus according to the first embodiment performs continuous imaging.

For example, in a case in which the mammography apparatus 10 according to this embodiment receives an imaging order and an imaging start command from the console 12, the CPU 20A of the control unit 20 executes the compression control processing program 21B stored in the ROM 20B to perform the compression control process whose example is illustrated in FIG. 8. FIG. 8 is a flowchart illustrating an example of the flow of the compression control process of the mammography apparatus 10 according to this embodiment. FIG. 9 is a timing chart illustrating an example of the operation of the compression control unit 80 and the imaging control unit 82 in a case in which the mammography apparatus 10 according to this embodiment performs the continuous imaging. Next, the flow of the compression control process of the compression control unit 80 will be described with reference to the timing chart illustrated in FIG. 9.

First, in Step S100 of FIG. 8, the compression control unit 80 determines whether the user has input a compression command through the operation unit 26. In a case in which the mammography apparatus 10 according to this embodiment captures a radiographic image, first, the user positions the breast of the subject on the imaging surface 40A of the imaging table 40 of the mammography apparatus 10. In a case in which the positioning is completed, the user inputs a compression command through the operation unit 26. In a case in which a compression command has not been input, the determination result in Step S100 is "No". On the other hand, in a case in which a compression command has been input, the determination result in Step S100 is "Yes" and the process proceeds to Step S102.

Then, in Step S102, the compression control unit 80 directs the compression plate driving unit 32 to move the compression plate 34 in the compression direction in response to the compression command such that the breast is compressed with the first compression force between the compression plate 34 and the imaging surface 40A of the imaging table 40. As illustrated in the timing chart of FIG. 9, in a case in which the movement of the compression plate 34 in the compression direction starts at a timing t100, the compression control unit 80 directs the compression plate driving unit 32 to move the compression plate 34 in the compression direction for a compression period until a timing t102 when the compression force of the compression plate 34 reaches the first compression force.

The compression of the breast by the compression plate 34 makes it possible to develop the overlap between the mammary gland tissues and to easily determine whether a lesion is a benign lesion or a malignant lesion. In addition, since the breast is compressed and fixed to the imaging table 40 by the compression plate 34, the body movement of the subject is suppressed. Therefore, it is possible to suppress the blurring of a radiographic image caused by the body movement. Further, since the breast is compressed by the compression plate 34, the thickness of the breast is reduced. Therefore, it is possible to reduce the amount of radiation emitted to the breast.

Then, in Step S104, the compression control unit 80 determines whether to perform the continuous imaging. For example, in a case in which the imaging order includes a command to perform the continuous imaging, the imaging control unit 82 according to this embodiment determines to perform the continuous imaging. In this embodiment, in a case in which the continuous imaging is performed, the tomosynthesis imaging is performed after the simple imaging is performed. In a case in which the continuous imaging is performed, the determination result in Step S104 is "Yes" and the process proceeds to Step S106.

In a case in which the breast is fixed by the compression plate 34, the user presses an irradiation command button included in the operation unit 56 of the console 12 to input a command to emit the radiation R. In a case in which the irradiation command is input, the imaging control unit 82 performs the simple imaging at a timing t203 under the control of the console 12 as illustrated in the timing chart of FIG. 9. Specifically, the imaging control unit 82 directs the radiation source 36R to emit the radiation R to the breast compressed by the compression plate 34. Then, the radiation detector 30 generates a two-dimensional image according to the radiation R transmitted through the breast. The image data of the captured two-dimensional image is transmitted to the console 12.

Then, in Step S106, the compression control unit 80 determines whether the simple imaging has ended. For example, in a case in which the image data indicating the two-dimensional image captured by the radiation detector 30 has been transmitted to the console 12, the compression control unit 80 according to this embodiment determines that the simple imaging has ended. However, a method for determining whether the simple imaging has ended is not limited to this embodiment. For example, a simple imaging end command input through the operation unit 56 of the console 12 may be received.

Until the simple imaging ends, the determination result in Step S106 is "No". On the other hand, in a case in which the simple imaging ends, the determination result in Step S106 is "Yes" and the process proceeds to Step S108.

In Step S108, the compression control unit 80 compresses the breast with the second compression force using the compression plate 34. Specifically, as illustrated in the timing chart of FIG. 9, in a case in which the compression plate driving unit 32 starts the movement of the compression plate 34 in the decompression direction at a timing t104, the compression control unit 80 stops the movement of the compression plate 34 at a timing t106 when the compression force detected by the compression force detection sensor 33 becomes the second compression force. In this embodiment, the period for which the compression force is changed from the first compression force to the second compression force, for example, the period from the timing t104 to the timing t106 in the example illustrated in FIG. 9 is referred to as a "change period".

The development of the mammary gland tissues may be little changed even in a case in which the compression force is reduced to the second compression force after the breast is compressed with the first compression force, which is disclosed in, for example, JP2017-225633A, JP2017-225634A, and JP2017-225635A. These patent publications disclose a technique in which, even in a case in which the compression plate 34 is moved in the decompression direction to reduce the compression force after the breast is compressed with the first compression force, it is difficult for the thickness of the breast to return to the original thickness due to the elasticity of the breast. Since it is difficult for the thickness of the breast to return to the original thickness and it is possible to maintain the thickness of the breast, the development of the mammary gland tissues is maintained or is little changed.

The second compression force may be lower than the first compression force in order to relieve the pain of the subject. In a case in which the compression force against the breast is too low, the thickness of the breast may return to the original thickness and the development of the mammary gland tissues may be different. In a case in which the development of the mammary gland tissues is different between the simple imaging (two-dimensional image) and the tomosynthesis imaging (projection image), for example, the position where calcification appears is changed, which is not preferable. In addition, in a case in which the compression force against the breast is too low, the body movement of the subject is likely to occur.

According to the above-mentioned patent publications, the second compression force is preferably 40% to 70% of the first compression force and is more preferably 50% of the first compression force. Alternatively, the second compression force is preferably 40 N to 100 N lower than the first compression force and is more preferably 50 N lower than the first compression force. In other words, the first compression force is preferably 143% to 250% of the second compression force and is more preferably 200% of the second compression force. Alternatively, the first compression force is preferably 40 N to 100 N higher than the second compression force and is more preferably 50 N higher than the second compression force. In addition, according to the above-mentioned patent publications, it is preferable that the second compression force is in the range of 40 N to 100 N in order to effectively relieve the pain of the subject and to suppress the body movement of the subject.

As in the example illustrated in FIG. 9, at a timing t205, the imaging control unit 82 directs the radiation source moving unit 37 to move the radiation source 36R of the radiation emitting unit 36 from an irradiation position t which is an imaging position in the simple imaging to an irradiation position t which is a tomosynthesis imaging start position. As described above, in the tomosynthesis imaging, there are the standard mode and the high resolution mode and the irradiation positions t which are the start positions in the two modes are different from each other. Therefore, the imaging control unit 82 moves the radiation source 36R to the irradiation position t which is the start position corresponding to each mode. The imaging control unit 82 stops the movement of the radiation source 36R at a timing t207 when the radiation source 36R reaches the irradiation position t which is the start position. As illustrated in FIG. 9, in this embodiment, the period from the timing t205 to the timing t207 is referred to as a "movement period" of the radiation source 36R.

As illustrated in FIG. 9, the movement period of the radiation source 36R after the end of the simple imaging overlaps with the change period for which the compression force of the compression plate 34 is changed from the first compression force to the second compression force. As such, in the mammography apparatus 10 according to this embodiment, the movement period of the radiation source 36R and the compression force change period at least partially overlap each other, which makes it possible to shorten the period for which the breast is continuously compressed.

In a case in which the breast is pressed with the second compression force by the compression plate 34 and the radiation source 36R is moved to the irradiation position tin the tomosynthesis imaging, as in the example illustrated in FIG. 9, the imaging control unit 82 performs the tomosynthesis imaging at a timing t209. Specifically, the radiation source moving unit 37 moves the radiation source 36R to each irradiation position t such that the breast compressed by the compression plate 34 is irradiated with the radiation R from the radiation source 36R at each irradiation position. Then, the radiation detector 30 generates a projection image for each irradiation position t according to the radiation R transmitted through the breast. The image data of a plurality of captured projection images is transmitted to the console 12.

Then, in Step S110, the compression control unit 80 determines whether the tomosynthesis imaging has ended. For example, in the radiography system 2 according to this embodiment, in a case in which the imaging ends, the user inputs a decompression command through the operation unit 26 of the mammography apparatus 10. Then, in a case in which the decompression command has been input through the operation unit 26, the compression control unit 80 determines to end the tomosynthesis imaging.

In a case in which the tomosynthesis imaging has not ended, that is, in a case in which the decompression command has not been input, the determination result in Step S110 is "No". On the other hand, in a case in which the tomosynthesis imaging has ended, that is, in a case in which the decompression command has been input, the determination result in Step S110 is "Yes" and the process proceeds to Step S118.

In Step S118, the compression control unit 80 releases the compression of the breast by the compression plate 34 and ends the compression control process. Specifically, as illustrated in the timing chart of FIG. 9, in a case in which the compression plate driving unit 32 starts the movement of the compression plate 34 in the decompression direction at a timing t108, the compression control unit 80 stops the movement of the compression plate 34 at a timing t110 when the compression plate 34 has been moved to a predetermined initial position. The predetermined position is a position where the compression of the breast is completely released. In this embodiment, the period required to release the compression of the breast, for example, the period from the timing t108 to the timing t110 in the example illustrated in FIG. 9 is referred to as a "release period".

In a case in which the imaging order includes a command to perform the continuous imaging, that is, in a case in which the imaging order includes a command to perform only the simple imaging or only the tomosynthesis imaging, the determination result in Step S104 is "No" and the process proceeds to Step S112. Hereinafter, in contrast to the continuous imaging, imaging in which only the simple imaging or only the tomosynthesis imaging is performed is referred to as "single imaging".

In Step S112, the compression control unit 80 determines whether the imaging order includes a command to perform the tomosynthesis imaging. In a case in which the imaging order includes the command to perform the tomosynthesis imaging, the determination result in Step S112 is "Yes" and the process proceeds to Step S114. In Step S114, the compression control unit 80 determines whether the tomosynthesis imaging has ended similarly to Step S110. The determination result in Step S114 is "No" until the tomosynthesis imaging ends. On the other hand, in a case in which the tomosynthesis imaging has ended, the determination result in Step S114 is "Yes" and the process proceeds to Step S118.

On the other hand, in a case in which the imaging order does not include the command to perform the tomosynthesis imaging, that is, in a case in which the imaging order includes a command to perform the simple imaging, the determination result in Step S112 is "No" and the process proceeds to Step S116. In Step S116, the compression control unit 80 determines whether the simple imaging has ended similarly to Step S106. The determination result in Step S116 is "No" until the simple imaging ends. On the other hand, in a case in which the simple imaging had ended, the determination result in Step S116 is "Yes" and the process proceeds to Step S118.

As such, in the compression control process of the mammography apparatus 10 according to this embodiment, in the continuous imaging in which the tomosynthesis imaging is performed after the simple imaging, after the simple imaging is performed with the breast compressed with the first compression force by the compression plate 34, the compression force is reduced from the first compression force to the second compression force. Then, the tomosynthesis imaging is performed in a state in which the breast is compressed with the second compression force. Therefore, according to the mammography apparatus 10 of this embodiment, it is possible to further effectively relieve the pain of the subject. In addition, according to the mammography apparatus 10 of this embodiment, it is possible to reduce the compression force in the tomosynthesis imaging in which the imaging time is likely to be shorter than that in the simple imaging. Therefore, it is possible to more effectively relieve the pain of the subject.

Second Embodiment

Next, a second embodiment will be described in detail.

In the first embodiment, the aspect in which the mammography apparatus 10 performs the simple imaging first and then performs the tomosynthesis imaging in the continuous imaging has been described. In contrast, in this embodiment, an aspect in which the mammography apparatus 10 performs the tomosynthesis imaging first and then performs the simple imaging in the continuous imaging will be described.

Since the overall configuration of a medical imaging system 1 (see FIG. 1) according to this embodiment and the configuration of a mammography apparatus 10 and a console 12 (see FIGS. 2 and 3) are the same as those in the first embodiment, the description thereof will not be repeated. In this embodiment, since the operation of the compression control unit 80 and the imaging control unit 82 of the mammography apparatus 10 and the compression control process of the compression control unit 80 are partially different from those in the mammography apparatus 10 according to the first embodiment, different operations and processes will be described.

Figure 10:
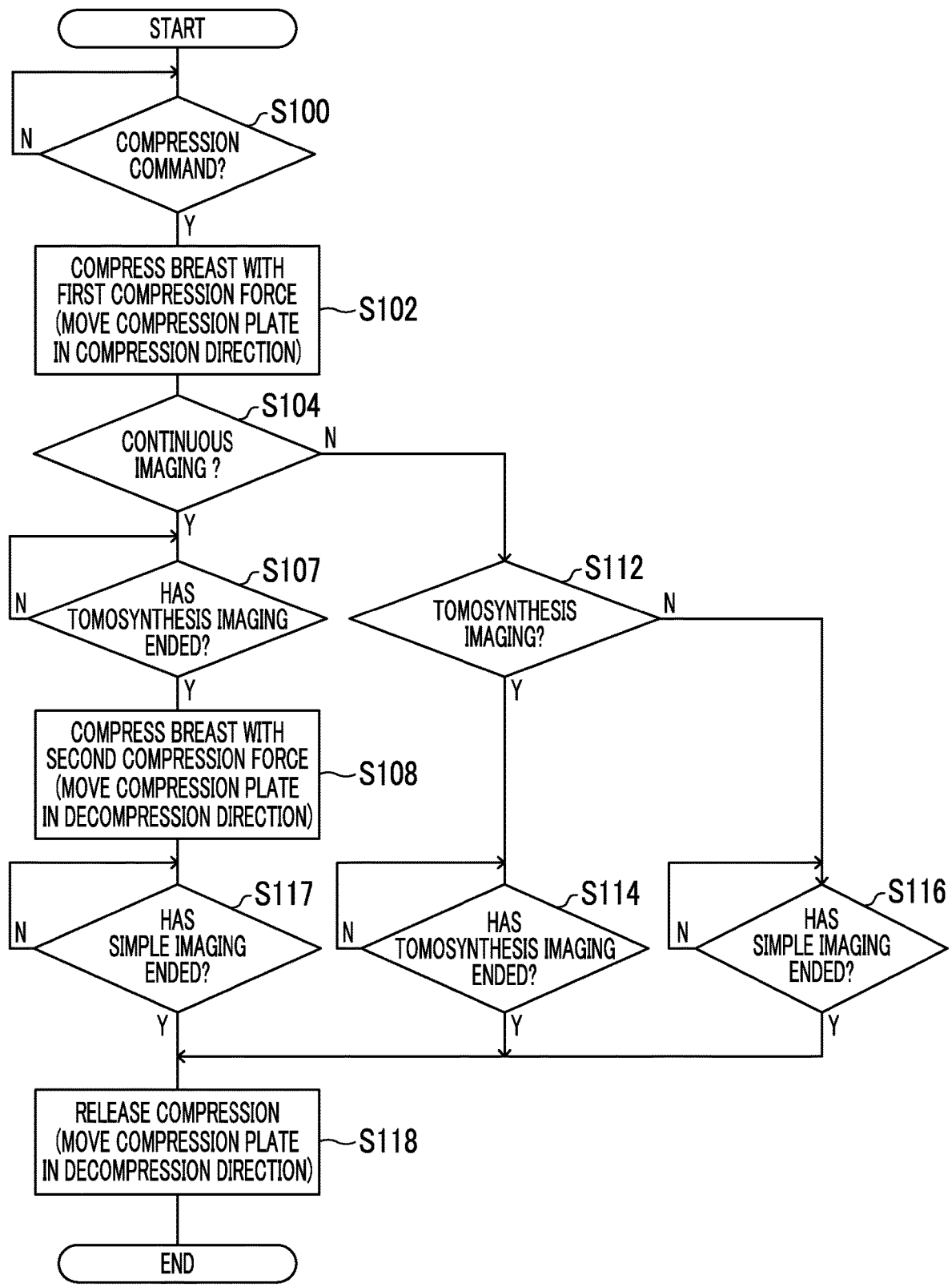
FIG. 10 is a flowchart illustrating an example of the flow of a compression control process of a mammography apparatus according to a second embodiment.
Figure 11:
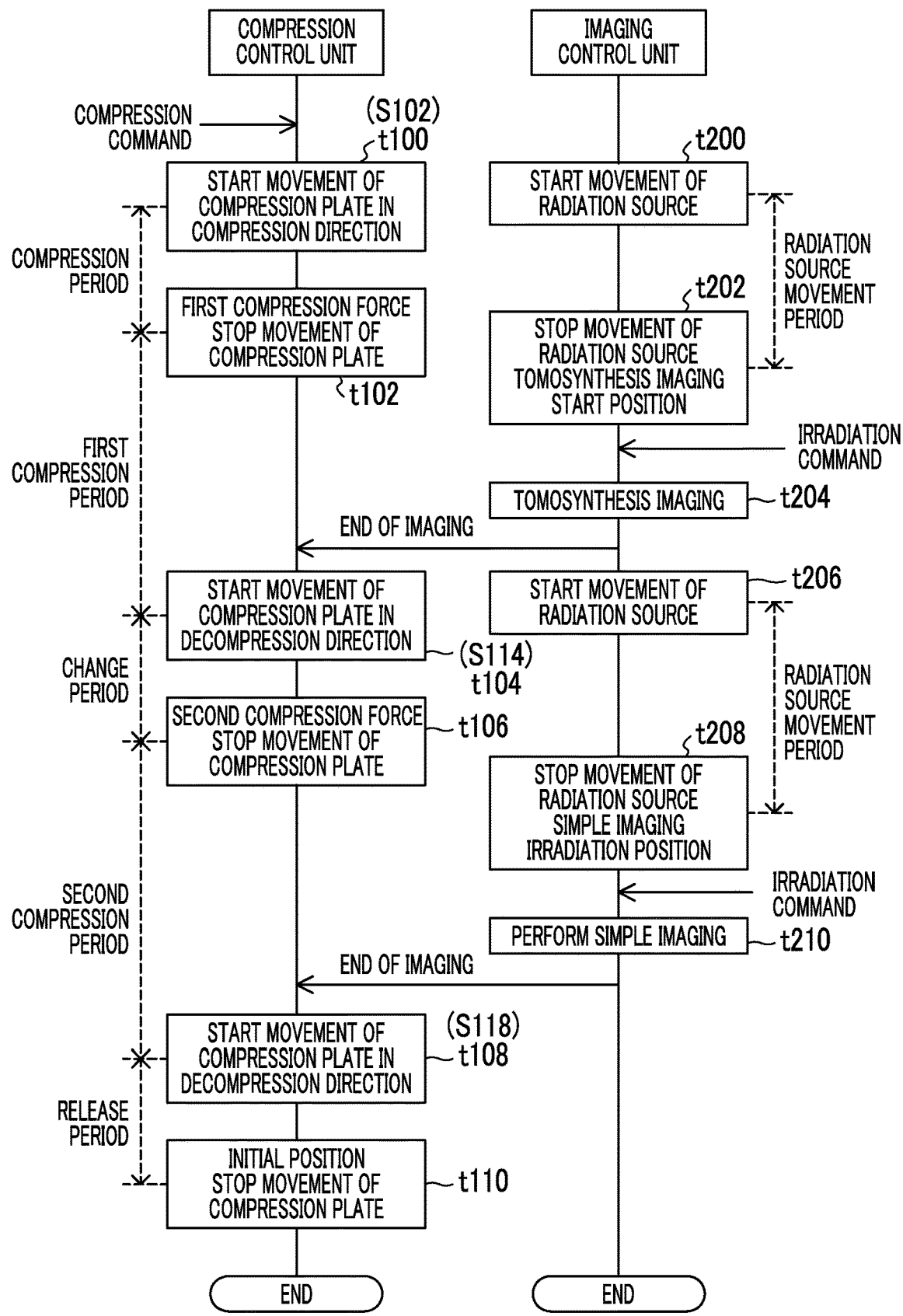
FIG. 11 is a timing chart illustrating an example of the operation of a compression control unit and an imaging control unit in a case in which the mammography apparatus according to the second embodiment performs continuous imaging.

In the mammography apparatus 10 according to this embodiment, for example, in a case in which an imaging order and an imaging start command are received from the console 12, the CPU 20A of the control unit 20 executes the compression control processing program 21B stored in the ROM 20B to perform the compression control process whose example has been described in FIG. 10. FIG. 10 is a flowchart illustrating an example of the flow of the compression control process of the mammography apparatus 10 according to this embodiment. FIG. 11 is a timing chart illustrating an example of the operation of the compression control unit 80 and the imaging control unit 82 in a case in which the mammography apparatus 10 according to this embodiment performs the continuous imaging. Next, the flow of the compression control process of the compression control unit 80 will be described with reference to the timing chart illustrated in FIG. 11.

As illustrated in FIG. 10, the compression control process according to this embodiment differs from the compression control process (see FIG. 8) according to the first embodiment in that it comprises Step S107 instead of Step S106 and comprises Step S117 instead of Step S110.

As illustrated in FIG. 10, in the compression control process according to this embodiment, in a case in which the continuous imaging is performed, that is, in a case in which the determination result in Step S104 is "Yes", the process proceeds to Step S107.

In a case in which the imaging order received from the console 12 includes a command to perform the continuous imaging, the imaging control unit 82 of the mammography apparatus 10 according to this embodiment directs the radiation source moving unit 37 to move the radiation source 36R of the radiation emitting unit 36 to an irradiation position t which is a tomosynthesis imaging start position in response to the imaging start command at a timing t200 of the timing chart whose example is illustrated in FIG. 11. As described above, in the tomosynthesis imaging, there are the standard mode and the high resolution mode and the irradiation positions t which are the start positions in the two modes are different from each other. Therefore, the imaging control unit 82 moves the radiation source 36R to the irradiation position t which is the start position corresponding to each mode. The imaging control unit 82 stops the movement of the radiation source 36R at a timing t202 when the radiation source 36R reaches the irradiation position t which is the start position. As illustrated in FIG. 11, in this embodiment, the period from the timing t200 to the timing t202 is referred to as a "movement period" of the radiation source 36R.

The imaging control unit 82 performs the tomosynthesis imaging at a timing t204 as described above under the control of the console 12 as illustrated in the timing chart of FIG. 11.

Then, in Step S107, the compression control unit 80 determines whether the tomosynthesis imaging has ended. Until the tomosynthesis imaging ends, the determination result in Step S107 is "No". On the other hand, in a case in which the tomosynthesis imaging ends, the determination result in Step S107 is "Yes" and the process proceeds to Step S108.

In Step S108, the compression control unit 80 compresses the breast with the second compression force using the compression plate 34 as described in the first embodiment. Specifically, as illustrated in the timing chart of FIG. 11, in a case in which the compression plate driving unit 32 starts the movement of the compression plate 34 in the decompression direction at a timing t104, the compression control unit 80 stops the movement of the compression plate 34 at a timing t106 when the compression force detected by the compression force detection sensor 33 becomes the second compression force.

As in the example illustrated in FIG. 11, immediately after the tomosynthesis imaging at the timing t204 ends, the imaging control unit 82 directs the radiation source moving unit 37 to move the radiation source 36R of the radiation emitting unit 36 from an irradiation position t which is a tomosynthesis imaging end position to an irradiation position t in the simple imaging at a timing t206. The imaging control unit 82 stops the movement of the radiation source 36R at a timing t208 when the radiation source 36R reaches the irradiation position t in the simple imaging. As illustrated in FIG. 11, in this embodiment, the period from the timing t206 to the timing t208 is referred to as a "movement period" of the radiation source 36R.

As illustrated in FIG. 11, the movement period of the radiation source 36R after the end of the tomosynthesis imaging overlaps with the change period for which the compression force of the compression plate 34 is changed from the first compression force to the second compression force. As such, in the mammography apparatus 10 according to this embodiment, the movement period of the radiation source 36R and the compression force change period at least partially overlap each other, which makes it possible to shorten the period for which the breast is continuously compressed.

In a case in which the radiation source 36R is moved to the irradiation position tin the simple imaging, the imaging control unit 82 performs the simple imaging at a timing t210 as described above under the control of the console 12, as illustrated in the timing chart of FIG. 11.

Then, in Step S117, the compression control unit 80 determines whether the simple imaging has ended. Until the simple imaging ends, the determination result in Step S117 is "No". On the other hand, in a case in which the simple imaging ends, the determination result in Step S117 is "Yes" and the process proceeds to Step S118.

As such, in the compression control process of the mammography apparatus 10 according to this embodiment, in the continuous imaging in which the simple imaging is performed after the tomosynthesis imaging, after the tomosynthesis imaging is performed with the breast compressed with the first compression force by the compression plate 34, the compression force is reduced from the first compression force to the second compression force. Then, the simple imaging is performed in a state in which the breast is compressed with the second compression force. Therefore, according to the mammography apparatus 10 of this embodiment, it is possible to further effectively relieve the pain of the subject.

In addition, according to the mammography apparatus 10 of this embodiment, for the movement period for which the imaging control unit 82 moves the radiation source 36R in order to perform the simple imaging after the tomosynthesis imaging, the compression control unit 80 changes the compression force of the compression plate 34 against the breast from the first compression force to the second compression force. In other words, the movement period of the radiation source 36R and the compression force change period at least partially overlap each other. Therefore, the overlap period increases and the period for which the breast is continuously compressed can be shortened, which makes it possible to more effectively relieve the pain of the subject.

Third Embodiment

Next, a third embodiment will be described in detail.

In this embodiment, an aspect in which a compression force control method that is performed after imaging that is performed later varies depending on whether the imaging that is performed later is the simple imaging or the tomosynthesis imaging in the continuous imaging will be described.

Since the overall configuration of a medical imaging system 1 (see FIG. 1) according to this embodiment and the configuration of a mammography apparatus 10 and a console 12 (see FIGS. 2 and 3) are the same as those in the first embodiment, the description thereof will not be repeated. In this embodiment, since a compression control process of the compression control unit 80 of the mammography apparatus 10 is partially different from that in the mammography apparatus 10 according to the first and second embodiments, different operations and processes will be described.

Figure 12:
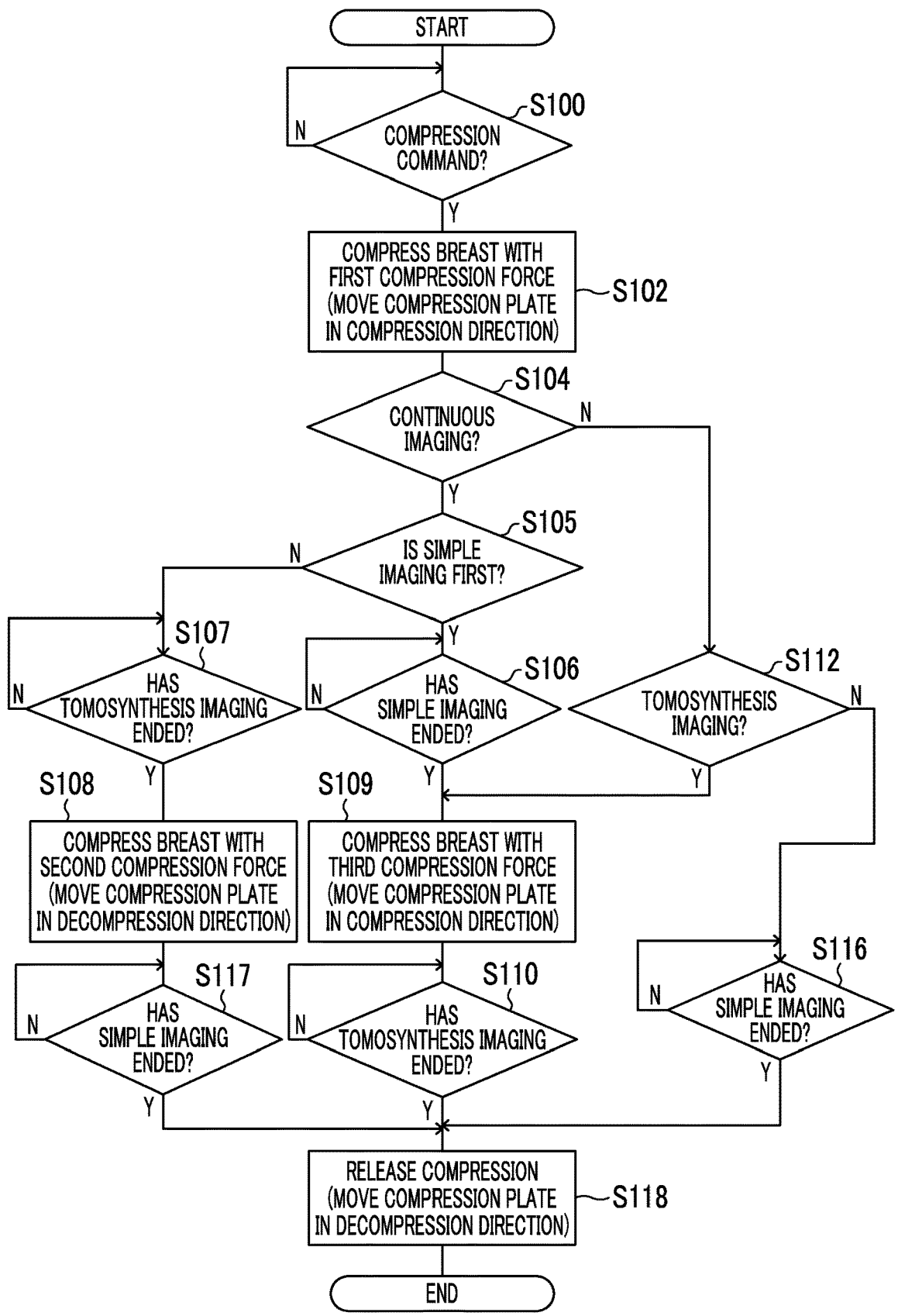
FIG. 12 is a flowchart illustrating an example of the flow of a compression control process of a mammography apparatus according to a third embodiment.

FIG. 12 is a flowchart illustrating an example of the flow of the compression control process in the mammography apparatus 10 according to this embodiment. As illustrated in FIG. 12, the compression control process according to this embodiment is a combination of the compression control process (see FIG. 8) according to the first embodiment and the compression control process (see FIG. 10) according to the second embodiment. The compression control process according to this embodiment differs from that in the first and second embodiments in that Step S105 is performed between Step S104 and Step S106.

In Step S105 illustrated in FIG. 12, the compression control unit 80 determines whether or not the imaging that is performed first in the continuous imaging is the simple imaging. For example, in the medical imaging system 1 according to this embodiment, the imaging order includes a command indicating which of the tomosynthesis imaging and the simple imaging is performed first. The compression control unit 80 determines whether or not to perform the simple imaging first on the basis of the command included in the imaging order.

In a case in which the imaging that is performed first is not the simple imaging, that is, in a case in which the imaging that is performed first is the tomosynthesis imaging, the determination result in Step S105 is "No" and the process proceeds to Step S107. Then, the continuous imaging is performed as in the compression control process according to the second embodiment. On the other hand, in a case in which the imaging that is performed first is the simple imaging, the determination result in Step S105 is "Yes" and the process proceeds to Step S106.

In addition, the compression control process according to this embodiment differs from that in the first and second embodiments in that Step S109 is performed between Step S106 and Step S110 instead of Step S108.

In a case in which the simple imaging ends, the compression control unit 80 compresses the breast with a third compression force higher than the first compression force using the compression plate 34 in Step S109. Specifically, the compression control unit 80 directs the compression plate driving unit 32 to move the compression plate 34 in the compression direction such that the breast is compressed with the third compression force by the compression plate 34.

In the tomosynthesis imaging, in a case in which the body of the subject moves for the period from the start to the end of the capture of a plurality of projection images, the quality of the projection image is likely to deteriorate, which is not preferable. In general, the imaging time in the tomosynthesis imaging is relatively long and is longer than that in the simple imaging. Therefore, the body movement tends to easily occur. For this reason, in the compression control process according to this embodiment, in a case in which the tomosynthesis imaging is performed, the compression force of the compression plate 34 is not lower than the first compression force and the breast is fixed by the compression plate 34 to suppress the movement of the subject. Therefore, in Step S109 of the compression control process illustrated in FIG. 12, the breast is compressed by the compression plate 34 with the third compression force higher than the first compression force.

In the compression control process according to this embodiment, in a case in which the determination result in Step S112 is "Yes", that is, in a case in which the single imaging is the tomosynthesis imaging, the process proceeds to Step S109.

As such, in the compression control process according to this embodiment, in a case in which the tomosynthesis imaging is performed, the compression force of the compression plate 34 against the breast is the third compression force higher than the first compression force. Therefore, the compression control process according to this embodiment makes it possible to suppress the body movement of the subject.

Figure 13:
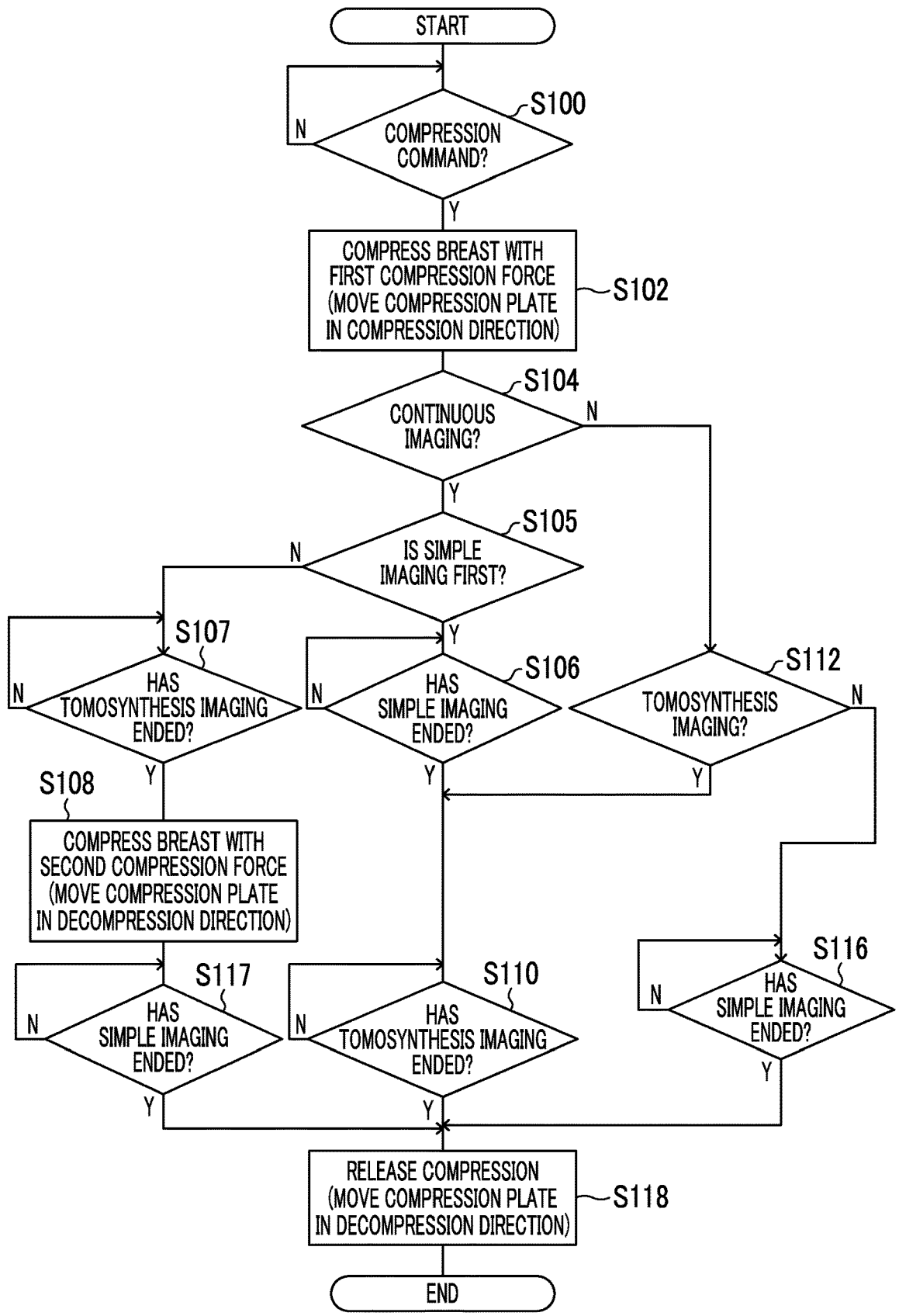
FIG. 13 is a flowchart illustrating another example of the flow of the compression control process of the mammography apparatus according to the third embodiment.

In the above-mentioned aspect, in the compression control process illustrated in FIG. 12, in a case in which the tomosynthesis imaging is performed, the breast is compressed by the compression plate 34 with the third compression force higher than the first compression force. However, the present disclosure is not limited to this aspect. FIG. 13 is a flowchart illustrating an example of the flow of a compression control process according to a modification example.

In the compression control process according to the modification example illustrated in FIG. 13, Step S109 of the compression control process (see FIG. 12) according to the above-mentioned embodiment is not provided.

Therefore, in a case in which the determination result in Step S106 is "Yes", that is, in a case in which the simple imaging has ended, the process proceeds to Step S110. In addition, in a case in which the determination result in Step S112 is "Yes", that is, in a case in which the single imaging is the tomosynthesis imaging, the process proceeds to Step S110.

As such, in the compression control process according to the modification example, in a case in which the tomosynthesis imaging is performed, the compression force of the compression plate 34 against the breast is maintained as the first compression force. In this case, in the compression control process, since the breast is compressed with the first compression force higher than the second compression force, it is also possible to suppress the body movement of the subject.

Further, in a case in which the continuous imaging in which the simple imaging and the tomosynthesis imaging are continuous performed is performed while the breast is compressed with the first compression force by the compression plate 34 in order to suppress the body movement of the subject, the entire imaging time increases. As a result, a burden on the subject increases. Therefore, in a case in which the continuous imaging is performed, at least in the simple imaging, the burden on the subject can be reduced by compressing the breast with the compression force lower than that in the tomosynthesis imaging using the compression plate 34.

Fourth Embodiment

Next, a fourth embodiment will be described in detail.

In this embodiment, an aspect in which, in the continuous imaging in which the tomosynthesis imaging is performed after the simple imaging, a compression force control method performed after imaging which is performed first varies depending on whether the imaging mode is the standard mode or the high resolution mode will be described.

Since the overall configuration of a medical imaging system 1 (see FIG. 1) according to this embodiment and the configuration of a mammography apparatus 10 and a console 12 (see FIGS. 2 and 3) are the same as those in the first embodiment, the description thereof will not be repeated. In this embodiment, since a compression control process of the compression control unit 80 of the mammography apparatus 10 is partially different from that in the mammography apparatus 10 according to the first and second embodiments, different operations and processes will be described.

Figure 14:
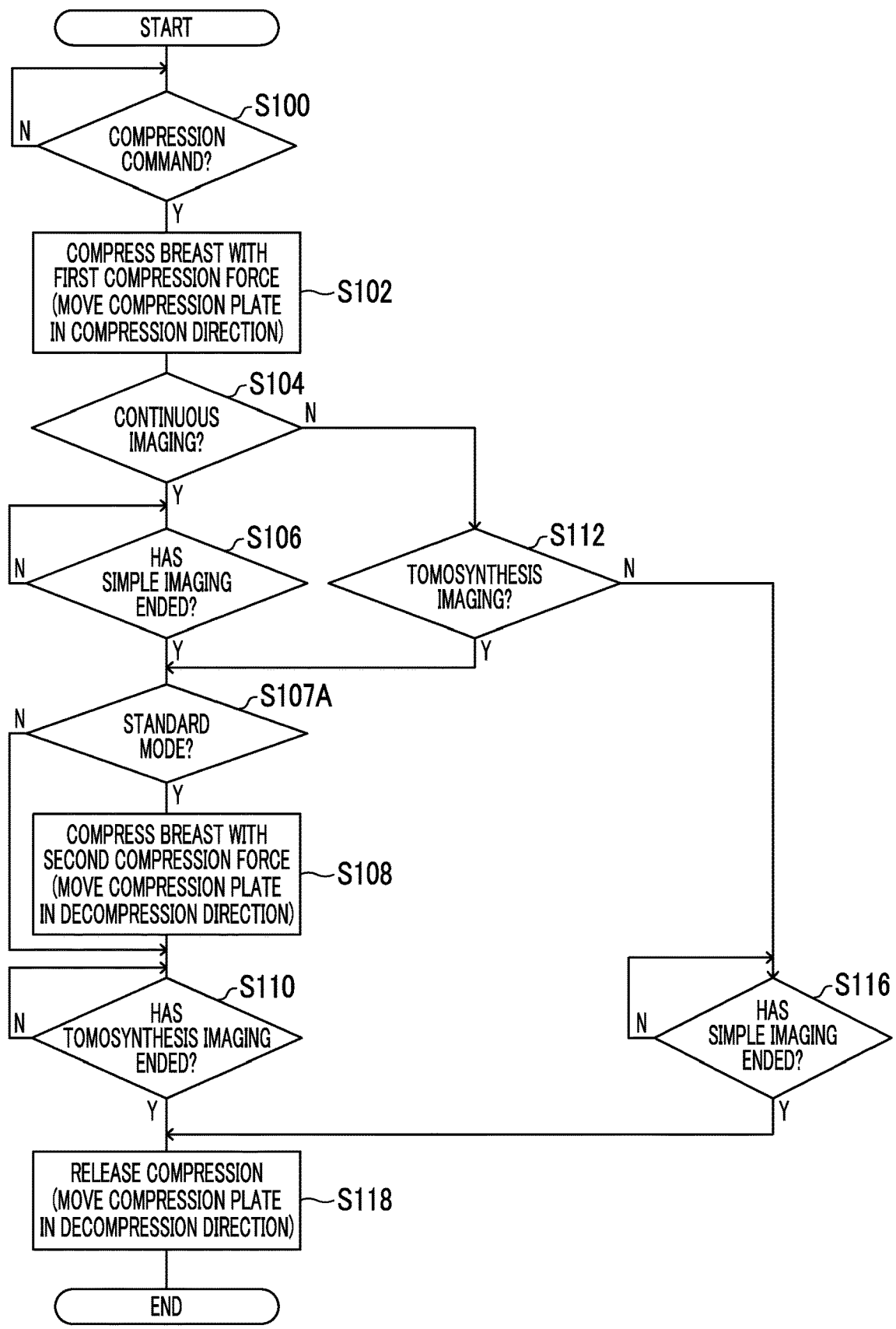
FIG. 14 is a flowchart illustrating an example of the flow of a compression control process of a mammography apparatus according to a fourth embodiment.

FIG. 14 is a flowchart illustrating an example of the flow of the compression control process in the mammography apparatus 10 according to this embodiment. As illustrated in FIG. 14, the compression control process according to this embodiment differs from the compression control process (see FIG. 8) according to the first embodiment in that Step S107A is performed between Step S106 and Step S108.

In Step S107A illustrated in FIG. 14, the compression control unit 80 determines whether or not the mode of the tomosynthesis imaging that is performed later in the continuous imaging is the standard mode. For example, in the medical imaging system 1 according to this embodiment, the imaging order includes a command indicating whether the mode of the tomosynthesis imaging is the standard mode or the high resolution mode. The compression control unit 80 determines whether or not the mode of the tomosynthesis imaging is the standard mode on the basis of the command included in the imaging order.

As described above, in the standard mode of the tomosynthesis imaging, the imaging time until all of a plurality of projection images are captured is shorter than that in the high resolution mode. In other words, in the high resolution mode, the imaging time until all of a plurality of projection images are captured is longer than that in the standard mode. Therefore, in the high resolution mode, the body movement of the subject is more likely to occur during imaging than that in the standard mode. For this reason, in the compression control process according to this embodiment, in a case in which the mode of the tomosynthesis imaging is the high resolution mode, the compression force of the compression plate 34 against the breast is maintained as the first compression force in order to suppress the body movement of the subject.

Therefore, in a case in which the mode of the tomosynthesis imaging is the standard mode, the determination result in Step S107A is "Yes" and the process proceeds to Step S108. On the other hand, in a case in which the mode of the tomosynthesis imaging is the high resolution mode, the determination result in Step S107A is "No" and the process proceeds to Step S110.

In the compression control process according to this embodiment, in a case in which the determination result in Step S112 is "Yes", that is, in a case in which the single imaging is the tomosynthesis imaging, the process proceeds to Step S107A.

As such, in the compression control process according to this embodiment, in a case in which the tomosynthesis imaging is performed, the imaging time is shorter than that in the standard mode. Therefore, the compression force of the compression plate 34 against the breast is changed from the first compression force to the second compression force and the tomosynthesis imaging is performed in a state in which the breast is compressed with the second compression force. In contrast, in the high resolution mode, since the imaging time is long, the compression force of the compression plate 34 against the breast is maintained as the first compression force in order to suppress the body movement of the subject and the tomosynthesis imaging is performed in a state in which the breast is compressed with the first compression force.

Fifth Embodiment

Next, a fifth embodiment will be described in detail.

In this embodiment, an aspect in which, in the continuous imaging, a compression force control method is different between a case in which an artifact, such as an implant, is included in the breast and a case in which the artifact is not included in the breast will be described.

Since the overall configuration of a medical imaging system 1 (see FIG. 1) according to this embodiment and the configuration of a mammography apparatus 10 and a console 12 (see FIGS. 2 and 3) are the same as those in the first embodiment, the description thereof will not be repeated. In this embodiment, since a compression control process of the compression control unit 80 of the mammography apparatus 10 is partially different from that in the mammography apparatus 10 according to the first and second embodiments, different operations and processes will be described.

Figure 15:
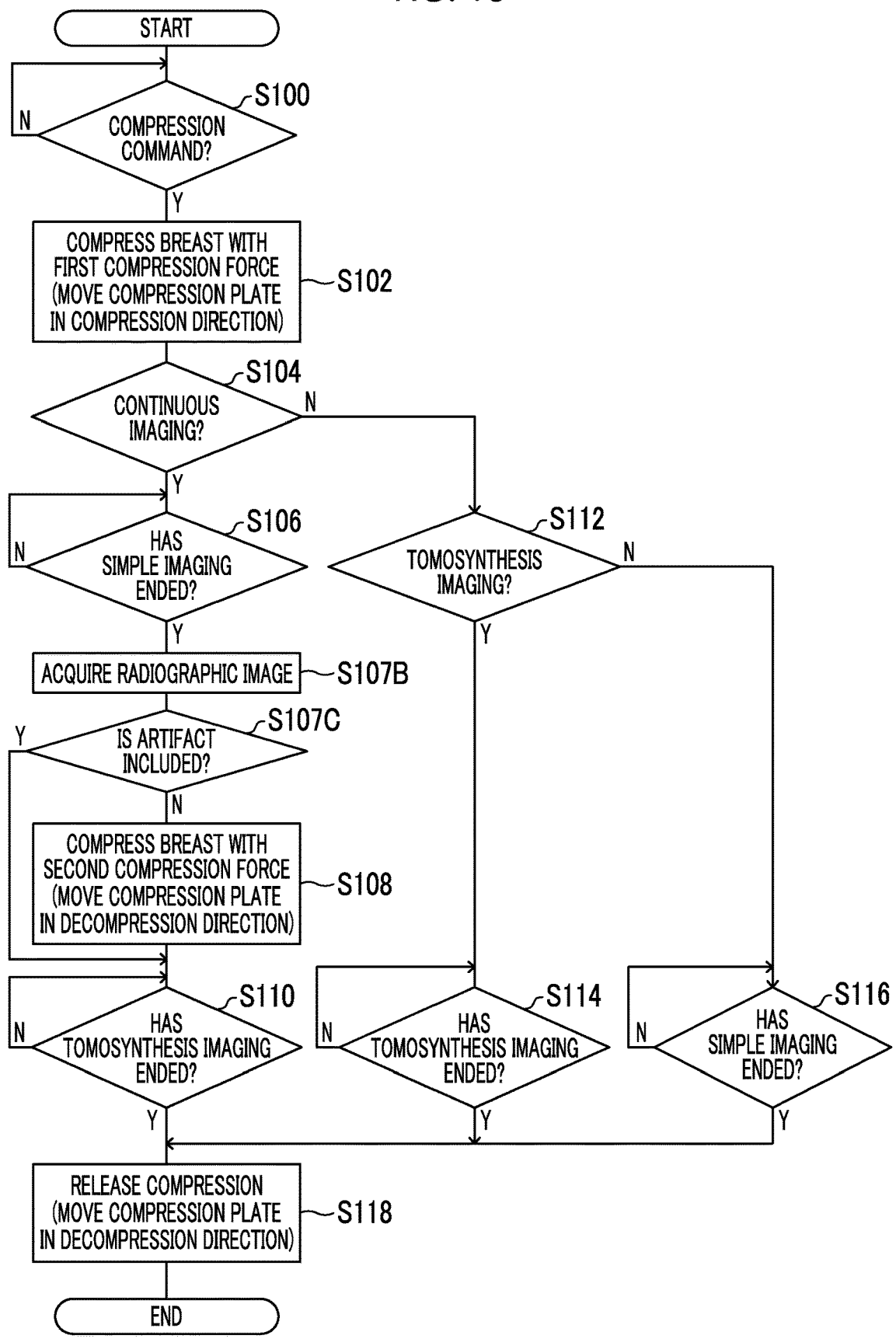
FIG. 15 is a flowchart illustrating an example of the flow of a compression control process of a mammography apparatus according to a fifth embodiment.

FIG. 15 is a flowchart illustrating an example of the flow of the compression control process in the mammography apparatus 10 according to this embodiment. As illustrated in FIG. 15, the compression control process according to this embodiment differs from the compression control process (see FIG. 8) according to the first embodiment in that Step S107B and Step S107C are performed between Step S106 and Step S108.

In Step S107B illustrated in FIG. 15, the compression control unit 80 acquires a radiographic image from the radiation detector 30. In this embodiment, the simple imaging is performed as the imaging that is performed first in the continuous imaging. Therefore, in Step S107B, the compression control unit 80 acquires a two-dimensional image from the radiation detector 30.

Then, in Step S107C, the compression control unit 80 determines whether an artifact, such as an implant, is included in the breast on the basis of the acquired radiographic image (two-dimensional image). For example, the compression control unit 80 can apply the known computer aided diagnosis (CAD) to estimate whether an artifact is included in the breast from the two-dimensional image.

In a case in which no artifacts are included in the breast, the determination result in Step S107C is "No" and the process proceeds to Step S108. On the other hand, in a case in which an artifact is included in the breast, the determination result in Step S107C is "Yes" and the process proceeds to Step S110.

In this embodiment, since the imaging that is performed first in the continuous imaging is the simple imaging, it is determined whether or not an artifact is present on the basis of the two-dimensional image obtained by the simple imaging. However, in a case in which the imaging that is performed first is the tomosynthesis imaging, at least one of the projection images obtained by the tomosynthesis imaging may be used instead of the two-dimensional image.

As such, in the compression control process according to this embodiment, in the continuous imaging, in a case in which it is estimated that an artifact is included in the breast on the basis of the radiographic image obtained by the imaging that is performed first, the compression force of the compression plate 34 against the breast is maintained as the first compression force and the imaging that is performed later in the continuous imaging is performed in a state in which the breast is compressed with the first compression force. On the other hand, in a case in which no artifacts are included in the breast, the compression force of the compression plate 34 against the breast is changed from the first compression force to the second compression force and the imaging that is performed later in the continuous imaging is performed in a state in which the breast is compressed with the second compression force.

Sixth Embodiment

Next, a sixth embodiment will be described in detail.

In each of the above-described embodiments, the aspect in which the compression force against the entire breast is an example of the force of compressing the breast according to the present disclosure has been described. However, in this embodiment, an aspect in which compression pressure that is compression force per unit area is an example of the force of compressing the breast according to the present disclosure will be described. In each of the above-described embodiments, the compression control unit 80 controls the compression force of the compression plate 34 against the breast. However, in this embodiment, the compression control unit 80 controls the compression pressure of the compression plate 34 against the breast.

Even in a case in which the breast is compressed with the same compression force, the pain of the subject with a large breast tends to be less than that of the subject with a small breast since the compression force is dispersed. For this reason, it is preferable to finely control the movement of the compression plate 34 according to the size of the breast. Therefore, the mammography apparatus 10 according to this embodiment controls the compression of the breast by the compression plate 34 on the basis of the compression pressure that is the compression force per unit area, instead of the compression force of the compression plate 34 against the entire breast.

Since the overall configuration (see FIG. 1) of a medical imaging system 1 according to this embodiment is the same as that in the first embodiment, the description thereof will not be repeated. In this embodiment, since the configuration of the mammography apparatus 10 is partially different from the configuration of the mammography apparatus 10 according to the first embodiment, the different configuration will be described.

Figure 16:
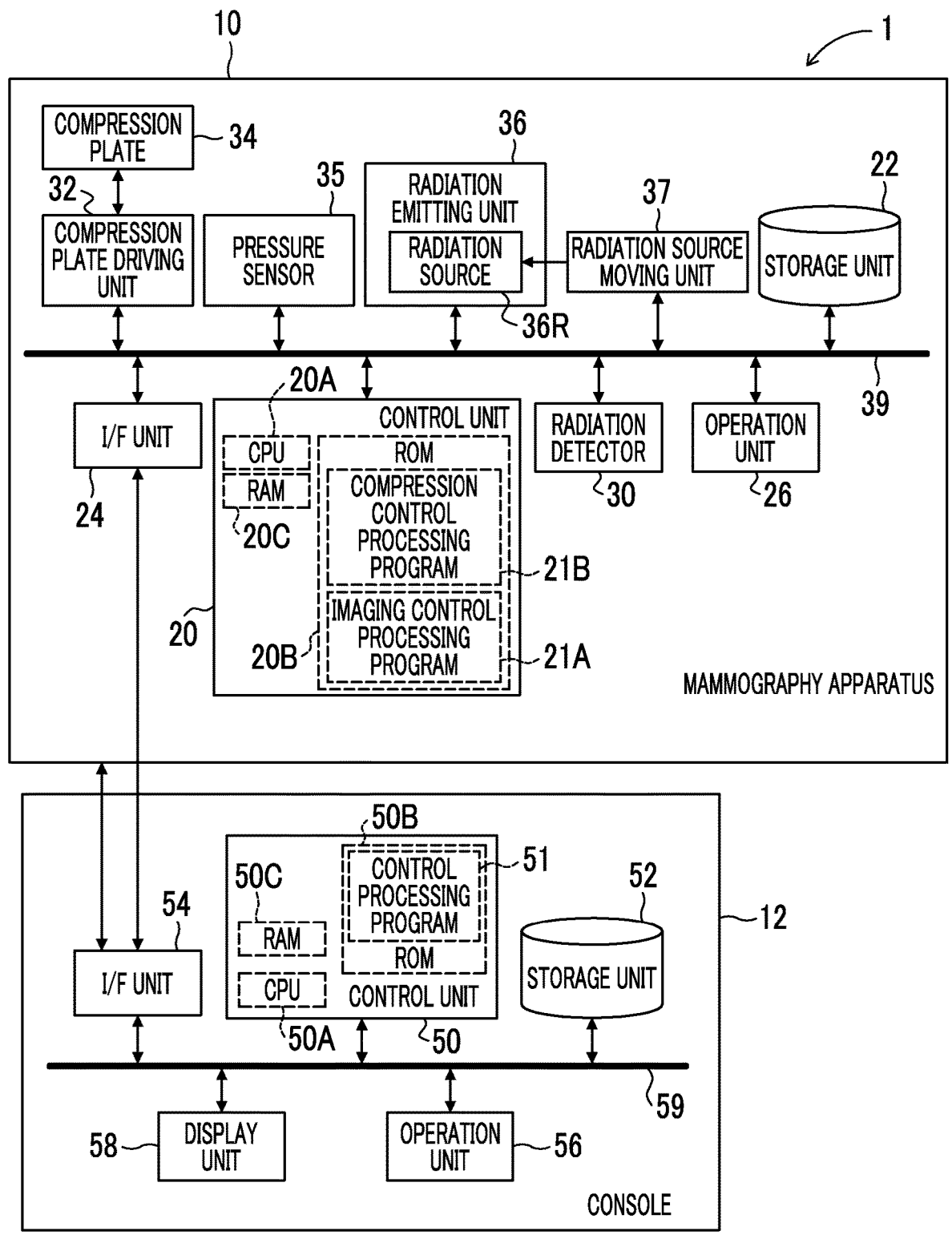
FIG. 16 is a block diagram illustrating an example of the configuration of a console and a mammography apparatus according to a sixth embodiment.

FIG. 16 is a block diagram illustrating an example of the configuration of the mammography apparatus 10 and the console 12 according to this embodiment. As illustrated in FIG. 16, the mammography apparatus 10 according to this embodiment differs from the mammography apparatus 10 according to the first embodiment in that it comprises a pressure sensor 35 instead of the compression force detection sensor 33.

Figure 17:
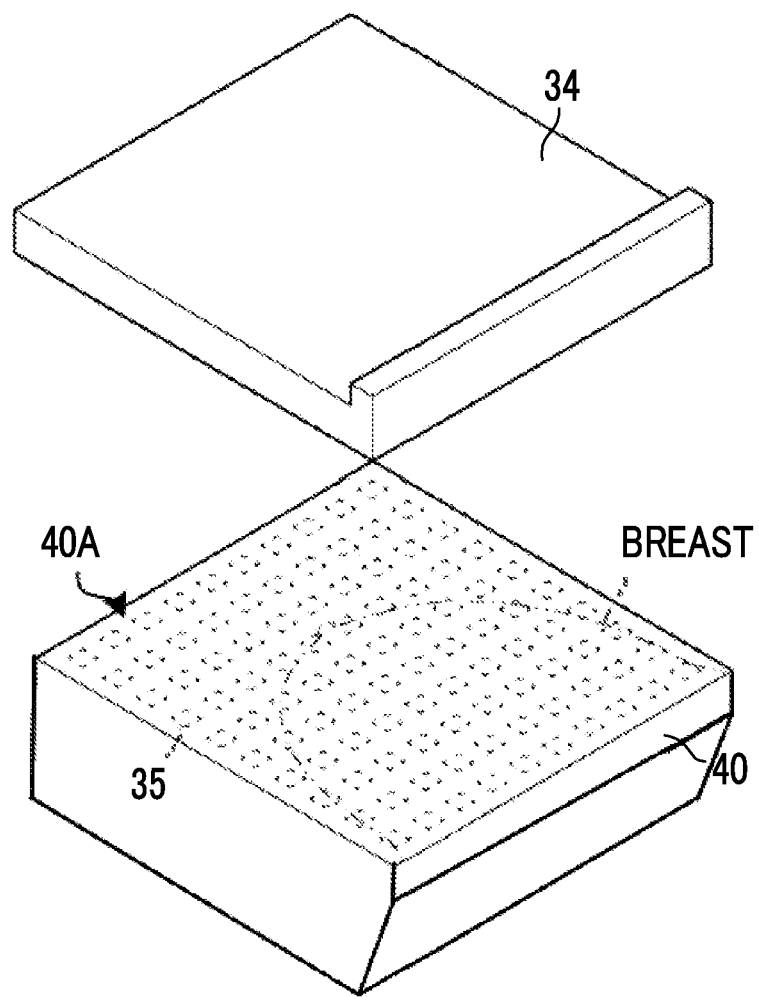
FIG. 17 is a diagram illustrating a pressure sensor.

As illustrated in FIG. 17, n (50 in this embodiment) pressure sensors 35 are two-dimensionally arranged on the imaging surface 40A of the imaging table 40 and each pressure sensor 35 detects the pressure applied to the imaging table 40 in a case in which the breast is compressed by the compression plate 34. The size of a region in which each pressure sensor 35 according to this embodiment detects pressure (the area of the imaging surface 40A; hereinafter, referred to as a "pressure detection area") is predetermined.

It is preferable that the pressure sensor 35 is made of a material which transmits the radiation R. In a case in which the pressure sensor 35 is made of a material which absorbs a portion of the radiation R, the image data of the acquired radiographic image is corrected according to the radiation transmittance of the pressure sensor 35.

Figure 18:
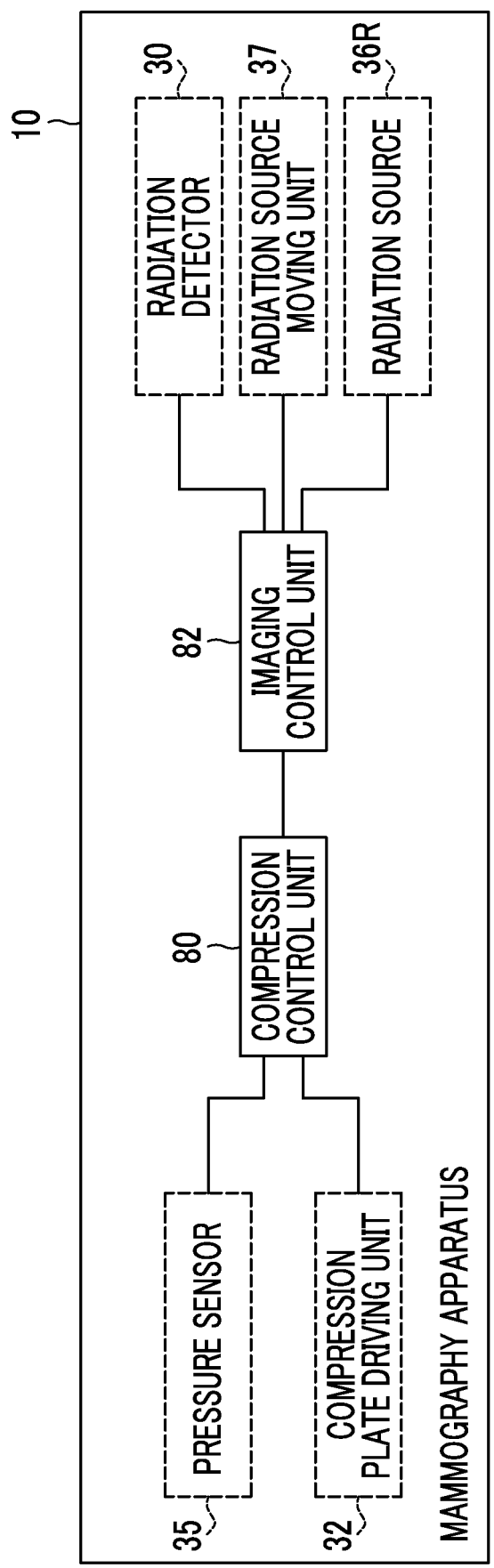
FIG. 18 is a functional block diagram illustrating an example of the function of the mammography apparatus according to the sixth embodiment.

FIG. 18 is a functional block diagram illustrating an example of the configuration of the mammography apparatus 10 according to this embodiment. As illustrated in FIG. 18, the mammography apparatus 10 according to this embodiment comprises the compression control unit 80 similarly to the mammography apparatus 10 (see FIG. 6) according to the first embodiment.

Information indicating the pressure which is the detection result of the pressure sensor 35 is input to the compression control unit 80 according to this embodiment. The compression control unit 80 outputs a command related to the movement of the compression plate 34 to the compression plate driving unit 32.

In a case in which the mammography apparatus 10 performs the continuous imaging in which the simple imaging and the tomosynthesis imaging are continuously performed for the breast in the compressed state, the compression control unit 80 performs control to set compression pressure which is the compression force of the compression plate 34 per unit area as a first compression pressure in one of the simple imaging and the tomosynthesis imaging which is performed first. After the one imaging, the compression control unit 80 performs control to change the compression pressure of the compression plate 34 from the first compression pressure to a second compression pressure lower than the first compression pressure. In the other of the simple imaging and the tomosynthesis imaging which is performed later, the compression control unit 80 performs control to set the compression pressure of the compression plate 34 against the breast as the second compression pressure.

The compression control unit 80 according to this embodiment derives the compression pressure on the basis of the detection results acquired from each pressure sensor 35. A method for deriving the compression pressure is not particularly limited. For example, the compression control unit 80 may select the maximum value from the detection results of the n pressure sensors 35 and may derive the compression pressure on the basis of the selected maximum value and the pressure detection area. For example, the compression control unit 80 may select a predetermined number of detection results in descending order from the detection results of the n pressure sensors 35 and may derive the compression pressure on the basis of the average value of the selected detection results and the pressure detection area. For example, since the detection results of the pressure sensors 35 provided in a portion of the imaging surface 40A with which the breast does not come into contact little change from 0 N/mm$^2$, the compression control unit 80 may derive the compression pressure on the basis of the pressure detection area and the average value of the detection results except 0 N/mm$^2$ or the detection results in a predetermined range from 0 N/mm$^2$ in consideration of errors. As such, it is preferable to derive the compression pressure using the detection results of the pressure sensors 35 provided in a portion of the imaging surface 40A with which the breast comes into contact.

The compression control unit 80 according to this embodiment repeatedly acquires the detection results of the pressure sensors 35 at a predetermined interval (0.1 seconds in this embodiment) and directs the compression plate driving unit 32 to move the compression plate 34 in the compression direction or the decompression direction until the compression pressure derived on the basis of the detection results of the pressure sensors 35 reaches the first compression pressure or the second compression pressure.

A compression control process of the compression control unit 80 in the mammography apparatus 10 according to this embodiment may be performed by changing the compression force in the compression control process (see FIG. 8) of the compression control unit 80 according to each of the above-described embodiments to the compression pressure.

Since the overall flow of the compression control process according to this embodiment and processes in each step are the same as those in each of the above-described embodiments, the description thereof will not be repeated.

Seventh Embodiment

Next, a seventh embodiment will be described in detail.

In this embodiment, a relationship between a grid movement period and a compression force change period in a mammography apparatus 10 comprising a grid will be described.

Since the overall configuration (see FIG. 1) of a medical imaging system 1 according to this embodiment is the same as that in the first embodiment, the description thereof will not be repeated. In this embodiment, since the configuration of the mammography apparatus 10 is partially different from the configuration of the mammography apparatus 10 according to the first embodiment, the different configuration will be described.

Figure 19:
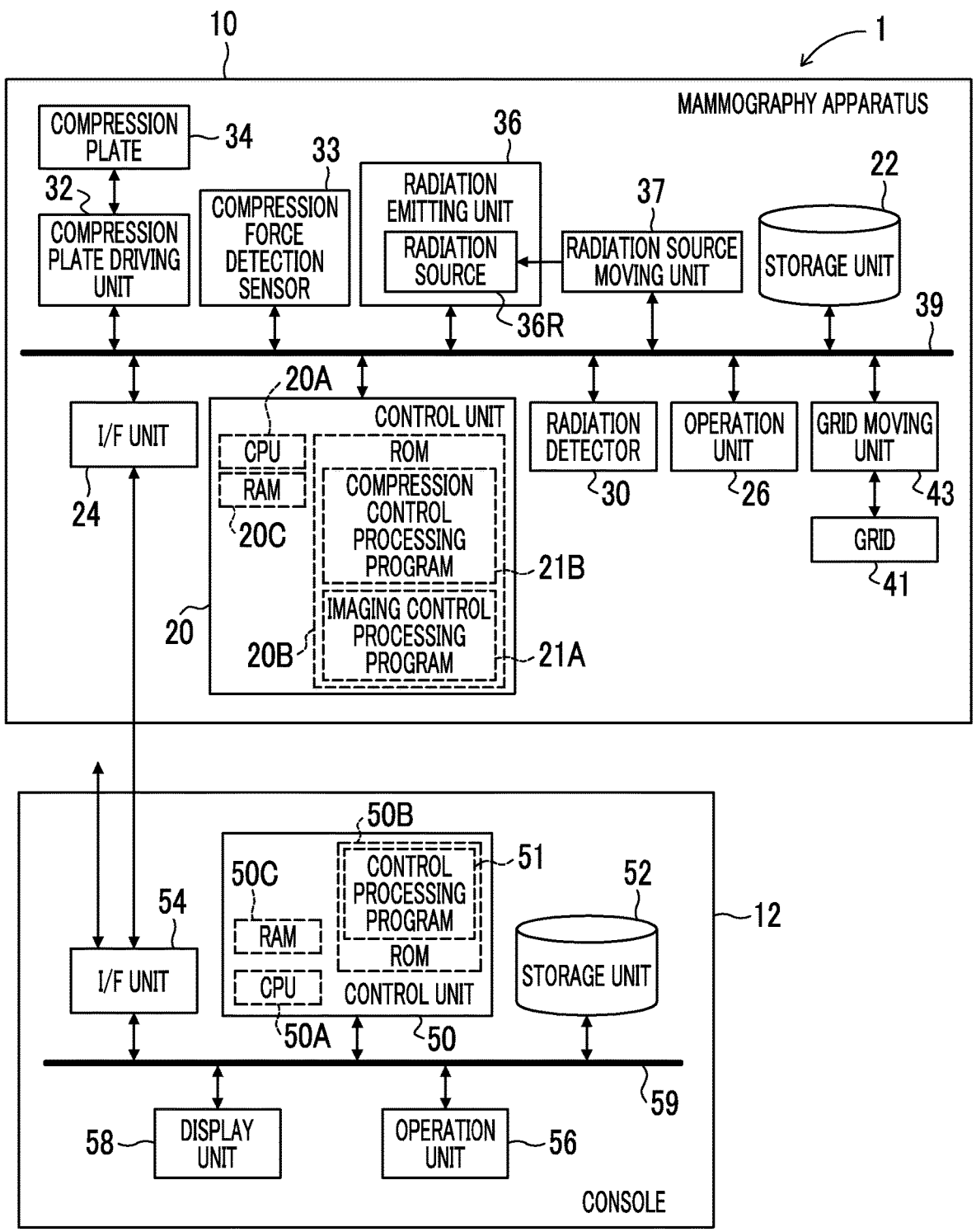
FIG. 19 is a block diagram illustrating an example of the configuration of a console and a mammography apparatus according to a seventh embodiment.

FIG. 19 is a block diagram illustrating an example of the configuration of the mammography apparatus 10 and the console 12 according to this embodiment. As illustrated in FIG. 19, the mammography apparatus 10 according to this embodiment differs from the mammography apparatus 10 (see FIG. 2) according to the first embodiment in that it comprises a grid 41 and a grid moving unit 43.

The grid 41 is provided in the imaging table 40 and removes scattered rays included in the radiation R transmitted through the breast which is an object. The grid moving unit 43 moves the grid 41 between a retracted position and a predetermined position under the control of the imaging control unit 82 (see FIGS. 6 and 18). The predetermined position in this embodiment is an example of a first position according to the present disclosure and the retracted position is an example of a second position according to the present disclosure.

In the mammography apparatus 10 according to this embodiment, in a case in which the simple imaging is performed, the grid 41 is disposed at the predetermined position between the radiation source 36R and the radiation detector 30. The scattered rays included in the radiation R transmitted through the breast are removed by the grid 41 disposed at the predetermined position and the radiation R from which the scattered rays have been removed is detected by the radiation detector 30. As such, the predetermined position is a position between the radiation source 36R and the radiation detector 30.

In contrast, in the tomosynthesis imaging of the mammography apparatus 10, since the irradiation angles at a plurality of irradiation positions t are different from each other, the grid 41 is not used in the imaging. Therefore, in the mammography apparatus 10, in a case in which the tomosynthesis imaging is performed, the grid 41 is disposed at the retracted position where it does not block a space between the radiation R emitted from the radiation source 36R and the radiation detector 30. As such, the retracted position is a position that is retracted from the radiation detector 30 as viewed from the radiation source 36R.

Next, the relationship between the control of the position of the grid 41 by the imaging control unit 82 and the control of the compression force by the compression control unit 80 will be described.

Figure 20:
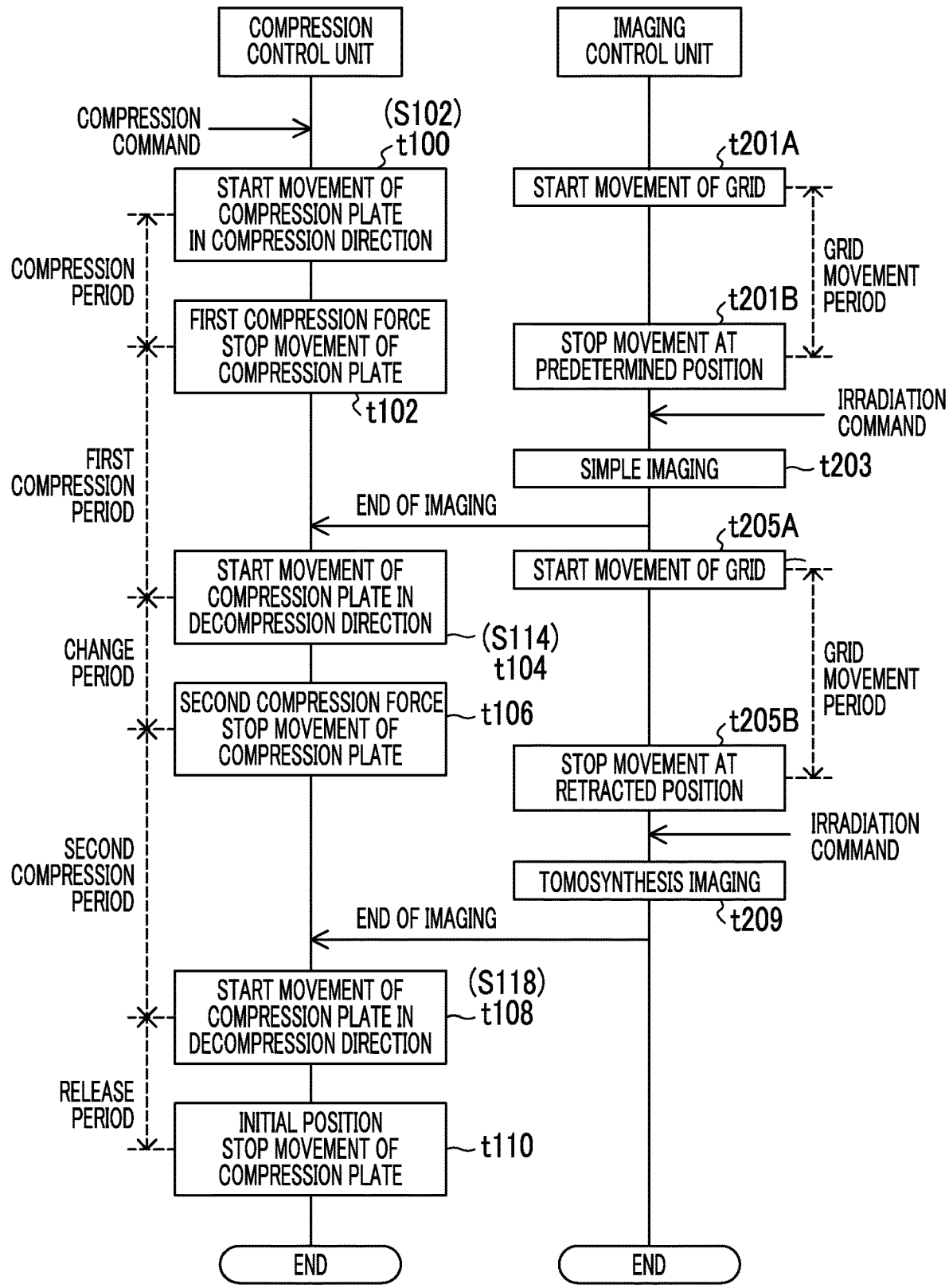
FIG. 20 is a timing chart illustrating an example of the operation of a compression control unit and an imaging control unit in a case in which the mammography apparatus according to the seventh embodiment performs continuous imaging.

First, the continuous imaging in which the single imaging is performed first and then the tomosynthesis imaging is performed will be described. A compression control process of the compression control unit 80 in the continuous imaging is the same as the compression control process (see FIG. 8) according to the first embodiment. FIG. 20 is a timing chart illustrating the control of the position of the grid 41 by the imaging control unit 82 and the control of the compression force by the compression control unit 80 in the continuous imaging.

At a timing t201A of the timing chart whose example is illustrated in FIG. 20, the imaging control unit 82 directs the grid moving unit 43 to start the movement of the grid 41 in response to an imaging start command. The grid moving unit 43 starts to move the grid 41 from the retracted position to the predetermined position. At a timing t201B, in a case in which the grid 41 reaches the predetermined position, the imaging control unit 82 stops the movement of the grid 41.

As illustrated in FIG. 20, for the grid movement period from the timing t201A to the timing t201B, the compression control unit 80 starts the movement of the compression plate 34 in the compression direction such that the breast is compressed with the first compression force by the compression plate 34. At least a portion of the compression period from a timing t100 to a timing t102 is the movement period of the grid 41 for which the grid 41 is moved to the predetermined position.

In a case in which the simple imaging at a timing t203 ends, the imaging control unit 82 directs the grid moving unit 43 to start the movement of the grid 41 at a timing t205A of the timing chart whose example is illustrated in FIG. 20 in order to continuously perform the tomosynthesis imaging. The grid moving unit 43 starts to move the grid 41 from the predetermined position to the retracted position. At a timing t205B, in a case in which the grid 41 reaches the retracted position, the imaging control unit 82 stops the movement of the grid 41.

As illustrated in FIG. 20, for the grid movement period from the timing t205A to the timing t205B, the compression control unit 80 starts the movement of the compression plate 34 in the decompression direction to change the compression force of the compression plate 34 from the first compression force to the second compression force. At least a portion of the change period from the timing t104 to the timing t106 is the movement period of the grid 41 for which the grid 41 is moved to the retracted position.

Figure 21:
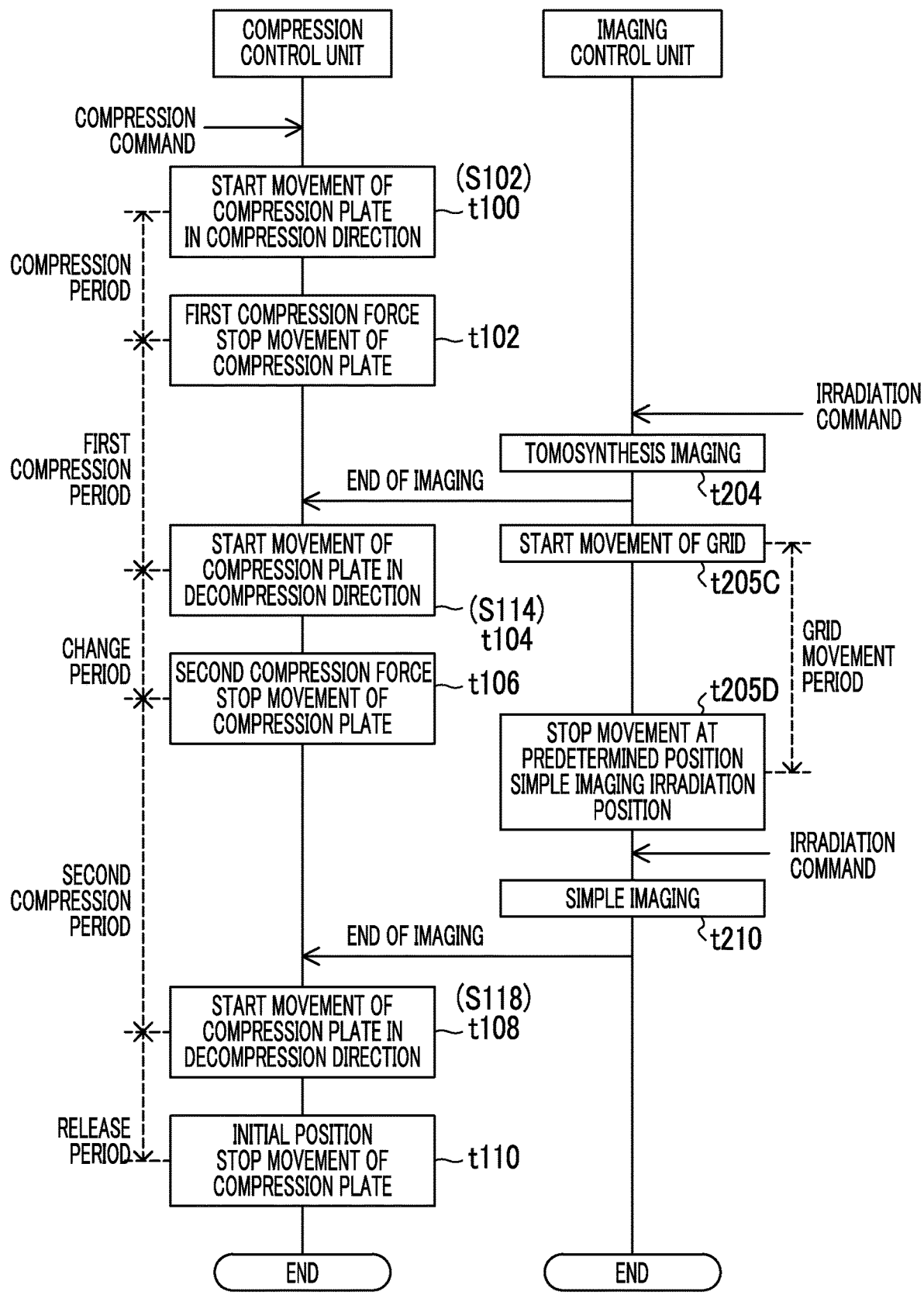
FIG. 21 is a timing chart illustrating another example of the operation of the compression control unit and the imaging control unit in a case in which the mammography apparatus according to the seventh embodiment performs continuous imaging.

Next, the continuous imaging in which the tomosynthesis imaging is performed first and then the simple imaging is performed will be described. A compression control process of the compression control unit 80 in the continuous imaging is the same as the compression control process (see FIG. 10) according to the second embodiment. FIG. 21 is a timing chart illustrating the control of the position of the grid 41 by the imaging control unit 82 and the control of the compression force by the compression control unit 80 in the continuous imaging.

In the continuous imaging, in a case in which the tomosynthesis imaging at the timing t204 ends, the imaging control unit 82 directs the grid moving unit 43 to start the movement of the grid 41 at a timing t205C of the timing chart whose example is illustrated in FIG. 21 in order to continuously perform the simple imaging. The grid moving unit 43 starts to move the grid 41 from the retracted position to the predetermined position. At a timing t205D, in a case in which the grid 41 reaches the predetermined position, the imaging control unit 82 stops the movement of the grid 41.

As illustrated in FIG. 21, for the grid movement period from the timing t205C to the timing t205D, the compression control unit 80 starts the movement of the compression plate 34 in the decompression direction to change the compression force of the compression plate 34 from the first compression force to the second compression force. At least a portion of the change period from the timing t104 to the timing t106 is the movement period of the grid 41 for which the grid 41 is moved to the retracted position.

As such, in the mammography apparatus 10 according to this embodiment, in a case in which the continuous imaging is performed, the movement period for which the grid 41 is moved between the predetermined position and the retracted position, the compression period for which the compression control unit 80 compresses the breast with the compression plate 34, and the change period for which the compression force against the breast is changed from the first compression force to the second compression force at least partially overlap each other. Therefore, according to the mammography apparatus 10 of this embodiment, since the movement period of the grid 41, the compression period for which the breast is compressed by the compression plate 34, and the compression force change period overlap each other, it is possible to shorten the period for which the breast is continuously compressed.

As described above, the radiography system 2 according to each of the above-described embodiments comprises the mammography apparatus 10. The mammography apparatus 10 comprises the radiation source 36R, the radiation detector 30, and the compression plate 34 that compresses the breast disposed between the radiation source 36R and the radiation detector 30 and can perform the simple imaging which irradiates the breast in the compressed state with the radiation R emitted from the radiation source 36R at a predetermined irradiation angle to capture a radiographic image and the tomosynthesis imaging which irradiates the breast in the compressed state with the radiation R emitted from the radiation source 36R at each of a plurality of irradiation angles to capture a projection image for each of the plurality of irradiation angles.

In addition, the mammography apparatus 10 comprises the compression control unit 80. In the case of the continuous imaging in which the simple imaging and the tomosynthesis imaging are continuously performed for the breast in the compressed state, in one of the simple imaging and the tomosynthesis imaging which is performed first, the compression control unit 80 performs control to set the compression force of the compression plate 34 against the breast as the first compression force. The compression control unit 80 performs control to change the compression force of the compression plate 34 from the first compression force to the second compression force lower than the first compression force after the one imaging and performs control to set the compression force of the compression plate 34 against the breast as the second compression force in the other of the simple imaging and the tomosynthesis imaging which is performed later.

Alternatively, in a case in which the continuous imaging in which the simple imaging and the tomosynthesis imaging are continuously performed for the breast in the compressed state, the compression control unit 80 performs control to set the compression pressure which is the compression force of the compression plate 34 per unit area as the first compression pressure in one of the simple imaging and the tomosynthesis imaging which is performed first. After the one imaging, the compression control unit 80 performs control to change the compression pressure of the compression plate 34 from the first compression pressure to the second compression pressure lower than the first compression pressure. In the other of the simple imaging and the tomosynthesis imaging which is performed later, the compression control unit 80 performs control to set the compression pressure of the compression plate 34 against the breast as the second compression pressure.

According to the above-mentioned configuration, in the mammography apparatus 10 according to the above-described embodiment, in a case in which the continuous imaging in which the simple imaging and the tomosynthesis imaging are continuously performed, after one of the simple imaging and the tomosynthesis imaging which is performed first, the compression force or the compression pressure of the compression plate 34 against the breast is reduced. In a case in which the compression force or the compression pressure is reduced, the other of the simple imaging and the tomosynthesis imaging is performed. Therefore, according to the mammography apparatus 10, it is possible to more effectively relieve the pain of the subject.

In the mammography apparatus 10 according to each of the above-described embodiments, in the one imaging that is performed first in the continuous imaging, the breast is compressed with the first compression force or the first compression pressure by the compression plate 34. Therefore, even in a case in which the compression force or the compression pressure is reduced to the second compression force or the second compression pressure, the development of the mammary gland tissues can be maintained by the elastic effect of the breast. As a result, the mammary gland region is the same in the two-dimensional image obtained by the simple imaging of the continuous imaging in the mammography apparatus 10 according to each of the above-described embodiments and the tomographic image based on the plurality of projection images obtained by the tomosynthesis imaging, which makes it easy to perform, for example, a diagnosis.

As such, in the compression control process of the mammography apparatus 10 according to this embodiment, in the continuous imaging in which the simple imaging is performed after the tomosynthesis imaging, after the tomosynthesis imaging is performed with the breast compressed with the first compression force by the compression plate 34, the compression force is reduced from the first compression force to the second compression force. Then, the simple imaging is performed in a state in which the breast is compressed with the second compression force. Therefore, according to the mammography apparatus 10 of this embodiment, it is possible to effectively relieve the pain of the subject.

In addition, according to the mammography apparatus 10 of this embodiment, for the movement period for which the imaging control unit 82 moves the radiation source 36R in order to perform the simple imaging after the tomosynthesis imaging, the compression control unit 80 changes the compression force of the compression plate 34 against the breast from the first compression force to the second compression force. In other words, the movement period of the radiation source 36R and the compression force change period at least partially overlap each other. Therefore, the overlap period increases and the period for which the breast is continuously compressed can be shortened, which makes it possible to more effectively relieve the pain of the subject.

The present disclosure is not limited to the compression control process of the compression control unit 80 according to each of the above-described embodiments. For example, in a case in which the continuous imaging is performed in response to a command from the subject, the compression force or the compression pressure may be changed from the first compression force or the first compression pressure to the second compression force or the second compression force after the imaging that is performed first. The compression state of the breast and the way of feeling pain vary depending on the subject. Therefore, an aspect in which the subject instructs whether to reduce the compression force or the compression pressure may be used. For example, in a case in which the subject operates the operation unit 26 of the mammography apparatus 10 to input a command to change the compression force or the compression pressure to the second compression force or the second compression pressure, the compression force or the compression pressure of the compression plate 34 against the breast may be changed from the first compression force or the first compression pressure to the second compression force or the second compression force in response to the command after the imaging that is performed first in the continuous imaging and before the imaging that is performed later starts as described above. In this case, even in a case in which the subject operates the operation unit 26 to input a command to reduce the compression during each of the simple imaging and the tomosynthesis imaging, it is preferable that the compression control unit 80 does not change the compression force or the compression pressure to the second compression force or the second compression pressure until the imaging that is being performed ends.

In each of the above-described embodiments, in a case in which the compression force or the compression pressure of the compression plate 34 is changed from the first compression force or the first compression pressure to the second compression force or the second compression pressure, the compression control unit 80 continuously reduces the compression force or the compression pressure. However, the present disclosure is not limited to each of the above-described embodiments. The overlap of the mammary gland tissues is developed by compressing the breast as described above. Therefore, the compression control unit 80 can change the compression force or the compression pressure to the extent that the overlap of the mammary gland tissues, that is, the development of the mammary gland tissues is not changed or the amount of change is within an allowable range even though the overlap is changed. For example, as the compressed state of the breast for the time from the start to the end of the continuous imaging, the breast may be continuously compressed to the extent that the area of the breast which comes into contact with the imaging surface 40A of the imaging table 40 is not changed. Therefore, the mammography apparatus 10 may reduce the compression against the breast according to the area of the breast which comes into contact with the imaging surface 40A after the imaging that is performed first in the continuous imaging and before the imaging that is performed later.

In each of the above-described embodiments, the mammography apparatus 10 comprises the compression control unit 80 and functions as the control device according to the present disclosure. However, the apparatus comprising some or all of the functions of the compression control unit 80 is not limited to each of the above-described embodiments. For example, another apparatus, such as the console 12, in the medical imaging system 1 may have some or all of the functions of the compression control unit 80 and may function as the control device according to the present disclosure.

In the mammography apparatus 10 according to each of the above-described embodiments, the radiation emitting unit 36 is moved to move the radiation source 36R to the irradiation position t. However, the mammography apparatus 10 is not limited to each of the above-described embodiments. For example, the mammography apparatus 10 may comprise a plurality of radiation sources 36R corresponding to each of the irradiation positions t.

In the mammography apparatus 10 according to each of the above-described embodiments, the radiation detector 30 may be a radiation detector having a function that detects radiation on the basis of charge (electric signal) generated by a sensor unit according to the emission of radiation R and, for example, starts or stops the accumulation of charge in each pixel of the radiation detector 30, which is called automatic exposure control (AEC). For example, in a case in which the radiation detector 30 has the AEC function in the continuous imaging, an operation using the AEC function may be performed during the imaging that is performed first in the continuous imaging and the result of the operation may be reflected in the imaging that is performed later in the continuous imaging.

In each of the above-described embodiments, for example, the following various processors can be used as the hardware structure of processing units performing various processes such as the compression control unit 80 and the imaging control unit 82. The various processors include, for example, a programmable logic device (PLD), such as a field-programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (program) to function as various processing units as described above.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the imaging processing program 21A and the compression control processing program 21B are stored (installed) in the ROM 20B in advance has been described. However, the present disclosure is not limited thereto. The imaging processing program 21A and the compression control processing program 21B may be recorded on a recording medium, such as a compact disk read only memory (CD-ROM), a digital versatile disk read only memory (DVD-ROM), or a universal serial bus (USB) memory, and then provided. In addition, the imaging processing program 21A and the compression control processing program 21B may be downloaded from an external apparatus through the network.

For example, the configurations and operations of the medical imaging system 1, the radiography system 2, and the mammography apparatus 10 described in each of the above-described embodiments are illustrative and may be changed according to the situation, without departing from the scope and spirit of the invention. In addition, the above-described embodiments may be appropriately combined with each other.

EXPLANATION OF REFERENCES

What is claimed is:

1. A radiography system comprising:
a mammography apparatus that includes
a radiation source,
a radiation detector, and
a compression member that compresses a breast disposed between the radiation source and the radiation detector,
the mammography apparatus being capable of performing simple imaging that irradiates the breast in a compressed state with radiation emitted from the radiation source at a predetermined irradiation angle to capture a radiographic image, and tomosynthesis imaging that sequentially irradiates the breast in the compressed state with the radiation emitted from the radiation source at each of a plurality of irradiation angles to capture a projection image for each of the plurality of irradiation angles; and
a control device including a compression control unit that, in a case of performing continuous imaging in which the simple imaging and the tomosynthesis imaging are continuously performed while the breast being compressed by the mammography apparatus, performs control to cause the compression member to compress the breast at a first force in a first imaging of the simple imaging or the tomosynthesis imaging that is performed first in the continuous imaging, to change a force of the compression member compressing the breast from the first force to a second force lower than the first force after the first imaging, and to cause the compression member to compress the breast at the second force in a second imaging that is performed later.

2. The radiography system according to claim 1, wherein the compression control unit performs control to change the force of compressing the breast from the first force to the second force after the tomosynthesis imaging in a case in which the simple imaging is performed after the tomosynthesis imaging in the continuous imaging.

3. The radiography system according to claim 1, wherein the compression control unit performs control to change the force of compressing the breast from the first force to the second force after the first imaging, in a case in which the second imaging is the tomosynthesis imaging in a first tomosynthesis imaging mode.

4. The radiography system according to claim 1, wherein the compression control unit further performs control to maintain the force of compressing the breast at the first force after the first imaging, instead of changing the force of compressing the breast from the first force to the second force after the first imaging, on the basis of at least one image of the radiographic image or the projection image captured by the mammography apparatus.

5. The radiography system according to claim 4, wherein, in a case in which it is estimated that an artifact is not included in the breast on the basis of the at least one image, the compression control unit performs control to change the force of compressing the breast from the first force to the second force after the first imaging, and in a case in which it is estimated that the artifact is included in the breast, the compression control unit performs control to maintain the force of compressing the breast at the first force after the first imaging, instead of changing the force of compressing the breast from the first force to the second force after the first imaging.

6. The radiography system according to claim 1, wherein, in a case in which the radiation source is moved after the first imaging and before the second imaging, a movement period of the radiation source and a change period for which the force of compressing the breast is changed after the first imaging overlap with each other.

7. The radiography system according to claim 1, wherein the mammography apparatus further comprises:
a grid that removes a scattered ray; and
a grid moving unit that moves the grid to a first position between the radiation source and the radiation detector in the simple imaging, and moves the grid to a second position that is different from the first position and that is retracted from the radiation detector as viewed from the radiation source in the tomosynthesis imaging, and
in the continuous imaging, a movement period for which the grid moving unit moves the grid from one position of the first position or the second position to another position and a change period for which the force of compressing the breast is changed after the first imaging overlap with each other.

8. The radiography system according to claim 7, wherein, in a case in which the tomosynthesis imaging is performed after the simple imaging in the continuous imaging, a movement period for which the grid moving unit moves the grid from the first position to the second position and the change period for which the force of compressing the breast is changed after the first imaging overlap with each other.

9. The radiography system according to claim 7, wherein, in a case in which the simple imaging is performed after the tomosynthesis imaging in the continuous imaging, a movement period for which the grid moving unit moves the grid from the second position to the first position and the change period for which the force of compressing the breast is changed after the first imaging overlap with each other.

10. The radiography system according to claim 1, wherein the compression control unit performs control to change the force from the first force to the second force by moving the compression member in a decompression direction.

11. The control device according to claim 1, wherein the force of compressing the breast is a compression force of compressing the entire breast,
the first force is a first compression force, and
the second force is a second compression force.

12. The control device according to claim 1, wherein the force of compressing the breast is a compression pressure that is a compression force per unit area,
the first force is a first compression pressure, and
the second force is a second compression pressure.

13. A radiography system comprising:
a mammography apparatus that includes
a radiation source,
a radiation detector, and a compression member that compresses a breast disposed between the radiation source and the radiation detector, the mammography apparatus being capable of performing simple imaging that irradiates the breast in a compressed state with radiation emitted from the radiation source at a predetermined irradiation angle to capture a radiographic image, and tomosynthesis imaging that sequentially irradiates the breast in the compressed state with the radiation emitted from the radiation source at each of a plurality of irradiation angles to capture a projection image for each of the plurality of irradiation angles; and a control device including a compression control unit that, in a case of performing continuous imaging in which the tomosynthesis imaging is performed after the simple imaging while the breast being compressed by the mammography apparatus, performs control to change the force of compressing the breast from a first force to a third force higher than the first force after the simple imaging and to cause the compression member to compress the breast at the third force in the tomosynthesis imaging, or performs control to maintain the force of compressing the breast at a first force after the simple imaging.

14. The radiography system according to claim 13, wherein the compression control unit performs control to maintain the force of compressing the breast at the first force after the simple imaging, in a case in which the tomosynthesis imaging is performed in a second tomosynthesis imaging mode having a wider irradiation angle range than a first tomosynthesis imaging mode.

15. A control method for controlling a mammography apparatus that includes a radiation source, a radiation detector, and a compression member that compresses a breast disposed between the radiation source and the radiation detector, the mammography apparatus being capable of performing simple imaging that irradiates the breast in the compressed state with radiation emitted from the radiation source at a predetermined irradiation angle to capture a radiographic image and tomosynthesis imaging that sequentially irradiates the breast in the compressed state with the radiation emitted from the radiation source at each of a plurality of irradiation angles to capture a projection image for each of the plurality of irradiation angles, the control method comprising:

in continuous imaging in which the mammography apparatus continuously performs the simple imaging and the tomosynthesis imaging for the breast in the compressed state, causing the compression member to compress the breast as at first force in a first imaging of the simple imaging or the tomosynthesis imaging that is performed first, changing the force of the compression member compressing the breast from the first force to a second force lower than the first force after the first imaging, and causing the compression member to compress the breast at the second force in a second imaging that is performed later.

16. The control method according to claim 15, wherein changing the force of compressing the breast from the first force to the second force after the tomosynthesis imaging is performed in a case in which the simple imaging is performed after the tomosynthesis imaging in the continuous imaging.

17. The control method according to claim 15, wherein changing the force of compressing the breast from the first force to the second force after the first imaging is performed in a case in which the second imaging is the tomosynthesis imaging in a first tomosynthesis imaging mode.

18. The control method according to claim 15, further comprising:

maintaining the force of compressing the breast at the first force after the first imaging, instead of changing the force of compressing the breast from the first force to the second force after the first imaging, on the basis of at least one image of the radiographic image or the projection image captured by the mammography apparatus.

19. The control method according to claim 18, further comprising:

in a case in which it is estimated that an artifact is not included in the breast on the basis of the at least one image, changing the force of compressing the breast from the first force to the second force after the first imaging, and in a case in which it is estimated that the artifact is included in the breast, maintaining the force of compressing the breast at the first force after the first imaging, instead of changing the force of compressing the breast from the first force to the second force after the first imaging.

20. The control method according to claim 15, wherein, in a case in which the radiation source is moved after the first imaging and before the second imaging, a movement period of the radiation source and a change period for which the force of compressing the breast is changed after the first imaging ends overlap each other.

21. The control method according to claim 15, further comprising:

moving a grid that is provided in the mammography apparatus and that removes a scattered ray to a first position between the radiation source and the radiation detector in the simple imaging; and moving the grid to a second position that is different from the first position and that is retracted from the radiation detector as viewed from the radiation source in the tomosynthesis imaging, wherein, in the continuous imaging, a movement period for which the grid is moved from one position of the first position or the second position to another position and a change period for which the force of compressing the breast is changed after the first imaging overlap with each other.

22. The control method according to claim 21, wherein, in a case in which the tomosynthesis imaging is performed after the simple imaging in the continuous imaging, a movement period for which the grid is moved from the first position to the second position and the change period for which the force of compressing the breast is changed after the first imaging overlap with each other.

23. The control method according to claim 21, wherein, in a case in which the simple imaging is performed after the tomosynthesis imaging in the continuous imaging, a movement period for which the grid is moved from the second position to the first position and the change period for which the force of compressing the breast is changed after the first imaging overlap with each other.

24. The control method according to claim 15,
wherein changing the force from the first force to the second force is performed by moving the compression member in a decompression direction.

25. The control method according to claim 15,
wherein the force of compressing the breast is a compression force of compressing the entire breast,
the first force is a first compression force, and
the second force is a second compression force.

26. The control method according to claim 15,
wherein the force of compressing the breast is a compression pressure which is a compression force per unit area,
the first force is a first compression pressure, and
the second force is a second compression pressure.

27. A control method for controlling a mammography apparatus that includes a radiation source, a radiation detector, and a compression member that compresses a breast disposed between the radiation source and the radiation detector, the mammography apparatus being capable of performing simple imaging that irradiates the breast in the compressed state with radiation emitted from the radiation source at a predetermined irradiation angle to capture a radiographic image and tomosynthesis imaging that sequentially irradiates the breast in the compressed state with the radiation emitted from the radiation source at each of a plurality of irradiation angles to capture a projection image for each of the plurality of irradiation angles, the control method comprising:
in continuous imaging in which the tomosynthesis imaging is performed after the simple imaging, changing the force of compressing the breast from a first force to a third force higher than the first force after the simple imaging and causing the compression member to compress the breast at the third force in the tomosynthesis imaging, or maintaining the force of compressing the breast at a first force after the simple imaging.

28. The control method according to claim 27,
wherein maintaining the force of compressing the breast at the first force after the simple imaging is performed in a case in which the tomosynthesis imaging is performed in a second tomosynthesis imaging mode having a wider irradiation angle range than a first tomosynthesis imaging mode.

29. A non-transitory storage medium storing a program that causes a computer to perform a control processing for controlling a mammography apparatus that includes a radiation source, a radiation detector, and a compression member that compresses a breast disposed between the radiation source and the radiation detector, the mammography apparatus being capable of performing simple imaging that irradiates the breast in the compressed state with radiation emitted from the radiation source at a predetermined irradiation angle to capture a radiographic image and tomosynthesis imaging that sequentially irradiates the breast in the compressed state with the radiation emitted from the radiation source at each of a plurality of irradiation angles to capture a projection image for each of the plurality of irradiation angles, the control processing comprising:
in continuous imaging in which the mammography apparatus continuously performs the simple imaging and the tomosynthesis imaging for the breast in the compressed state, causing the compression member to compress the breast at a first force in a first imaging of the simple imaging or the tomosynthesis imaging that is performed first,
changing the force of the compression member compressing the breast from the first force to a second force lower than the first force after the first imaging, and causing the compression member to compress the breast at the second force in a second imaging that is performed later.

* * * * *